(12) United States Patent
Lu et al.

(10) Patent No.: US 12,338,205 B2
(45) Date of Patent: *Jun. 24, 2025

(54) CRYSTALLINE FORM OF 3-((L-VALYL)AMINO)-1-PROPANESULFONIC ACID

(71) Applicant: RISEN (SUZHOU) PHARMA TECH CO., LTD., Jiangsu (CN)

(72) Inventors: Jiasheng Lu, Suzhou (CN); Jiamin Gu, Suzhou (CN); Xiang Ji, Suzhou (CN); Xinyong Lv, Suzhou (CN); Juan Peng, Suzhou (CN); Xianqi Kong, Suzhou (CN)

(73) Assignee: RISEN (SUZHOU) PHARMA TECH CO., LTD., Suzhou (CN)

( * ) Notice: Subject to any disclaimer, the term of this patent is extended or adjusted under 35 U.S.C. 154(b) by 903 days.

This patent is subject to a terminal disclaimer.

(21) Appl. No.: 17/293,742

(22) PCT Filed: Oct. 30, 2019

(86) PCT No.: PCT/CN2019/114212
§ 371 (c)(1),
(2) Date: May 13, 2021

(87) PCT Pub. No.: WO2020/098492
PCT Pub. Date: May 22, 2020

(65) Prior Publication Data
US 2022/0002239 A1    Jan. 6, 2022

(30) Foreign Application Priority Data

Nov. 13, 2018 (CN) .......................... 201811347491.1

(51) Int. Cl.
*C07C 309/15* (2006.01)
*A61P 25/28* (2006.01)

(52) U.S. Cl.
CPC ............ *C07C 309/15* (2013.01); *A61P 25/28* (2018.01); *C07B 2200/13* (2013.01)

(58) Field of Classification Search
None
See application file for complete search history.

(56) References Cited

U.S. PATENT DOCUMENTS 11,186,543 B2 * 11/2021 Lu ............................ A61P 25/28
11,608,314 B2 * 3/2023 Lu ............................ A61P 9/14

FOREIGN PATENT DOCUMENTS

WO    2009019534 A2    2/2009
WO    2018170590 A1    9/2018

OTHER PUBLICATIONS

Kumar et al., Materials Chemistry and Physics, vol. 108, Issues 2-3, 2008, pp. 359-363 (Year: 2008).*
Merz et al., Cryst. Growth Des. 2015, 15, 4, 1553-1558 (Year: 2015).*
Supplementary European Search Report issued in corresponding European application No. 19884193.4 on Jul. 13, 2022.

(Continued)

*Primary Examiner* — Jeffrey S Lundgren
*Assistant Examiner* — Anthony Joseph Seitz
(74) *Attorney, Agent, or Firm* — BCF LLP

(57) ABSTRACT

The present invention relates to a crystalline form of compound 3-((L-valyl)amino)-1-propanesulfonic acid, preparation method and uses thereof.

20 Claims, 12 Drawing Sheets

(56) References Cited

OTHER PUBLICATIONS

International Search Report and Written Opinion issued in corresponding International application No. PCT/CN2019/114212 on Feb. 3, 2020.
Shi et al., Geometric isotope effect of deuteration in a hydrogen-bonded host-guest crystal, Nature Communications, 2018, 9:481, p. 1-9.
Crawford et al., Isotopic Polymorphism in Pyridine, Low-Temperature Polumorphs, Angew. Chem. Int. Ed. 2009, 48, 755-757.
Merz et al., Deuterium perturbs the molecular arrangement in the solid state, ACS Publications, American Chemical Society, Cryst. Growth Des. 2015, 15, 1553-1558.

\* cited by examiner

CRYSTALLINE FORM OF 3-((L-VALYL) AMINO)-1-PROPANESULFONIC ACID

CROSS-REFERENCE TO RELATED APPLICATIONS

This application is a U.S. National Stage Application under 35 U.S.C. § 371 of International Application No. PCT/CN2019/114212, filed Oct. 30, 2019, which claims priority to Chinese Application No. 201811347491.1, filed Nov. 13, 2018, the entire contents of each of which are hereby incorporated by reference.

TECHNICAL FIELD

The present invention relates to a crystalline form of compound 3-((L-valyl)amino)-1-propanesulfonic acid, preparation method and uses thereof.

BACKGROUND

The compound 3-((L-valyl)amino)-1-propanesulfonic acid is known to be useful for treatment of an amyloid-β related disease.

At present, there has been no report on parameters of the compound 3-((L-valyl)amino)-1-propanesulfonic acid, such as a crystalline form and a crystalline melting point.

As a result, there is a need to develop a crystalline form of 3-((L-valyl)amino)-1-propanesulfonic acid, which crystalline form has advantages of high purity, simple preparation process, good thermodynamic stability, low hygroscopicity, good flow properties, compliance with quality requirements of pharmaceutical preparations, and long-term preservation.

SUMMARY OF THE INVENTION

The present invention pertains to a novel crystalline form of compound 3-((L-valyl)amino)-1-propanesulfonic acid (hereinafter also referred to as Crystalline Form I), which crystalline form has advantages of higher purity, simpler preparation process, better thermodynamic stability, lower hygroscopicity, better flow properties, better reproducibility in manufacturing, compliance with quality requirements of pharmaceutical preparations, long-term preservation, and can be applied to production of formulations.

One aspect of the present invention provides a crystalline form of compound 3-((L-valyl)amino)-1-propanesulfonic acid. The crystalline form exhibits characteristic diffraction peaks at 2θ diffraction angles of 9.4°, 11.1°, 15.9°, 17.8°, 18.4°, 21.0°, and 22.5° in an X-ray powder diffraction pattern using Cu-Kα as a radiation source, wherein 2θ has an error range of ±0.2°.

In an embodiment, preferably, said crystalline form exhibits characteristic diffraction peaks at 2θ diffraction angles of 9.4°, 11.1°, 14.9°, 15.9°, 16.6°, 17.8°, 18.4°, 19.5°, 21.0°, 22.5°, 23.1°, and 25.7° in the X-ray powder diffraction pattern, wherein 2θ has an error range of ±0.2°.

In an embodiment, preferably, said crystalline form exhibits characteristic diffraction peaks at 2θ diffraction angles of 9.4°, 11.1°, 14.9°, 15.9°, 16.6°, 17.8°, 18.4°, 19.5°, 21.0°, 21.6°, 22.5°, 23.1°, 25.7°, 26.4°, 26.9°, 30.4°, 32.4°, and 34.5° in the X-ray powder diffraction pattern, wherein 2θ has an error range of ±0.2°.

In an embodiment, preferably, said crystalline form (substantially) has an X-ray powder diffraction pattern as shown in FIG. 2.

In an embodiment, said crystalline form has a space group of $P4_32_12$, unit cell dimensions: a=11.1988(4) Å, α=90°, b=11.1988(4) Å, β=90°, c=18.2429(7) Å, γ=90°, Z=8, and has a unit cell volume of 2287.90(19) Å$^3$.

In an embodiment, said crystalline form belongs to a tetragonal system.

In an embodiment, said crystalline form has a crystal size of 0.300×0.300×0.100 mm$^3$.

In an embodiment, a starting melt temperature of a differential scanning calorimetry curve of said crystalline form is about 301° C. or higher. In another embodiment, a starting melt temperature of a differential scanning calorimetry curve of said crystalline form is about 301° C. to about 312° C. In further embodiment, a starting melt temperature of a differential scanning calorimetry curve of said crystalline form may be about 301° C., about 305° C., about 306° C., about 307° C., about 308° C., about 309° C., or about 312° C.

In an embodiment, the morphology of said crystalline form may be slices, blocks, particles, bulks, fine particles or fine powder.

Another aspect of the present invention provides Embodiment 1): a method for preparing the Crystalline Form I of compound 3-((L-valyl)amino)-1-propanesulfonic acid, said method comprising the following steps: adding a solvent system to the compound 3-((L-valyl)amino)-1-propanesulfonic acid to obtain a clear solution, and volatilizing to dryness to obtain the Crystalline Form I, wherein the step of adding the solvent system comprises (or consisting of):

adding the solvent system consisting of a first solvent, wherein said first solvent is water; or adding the solvent system consisting of a first solvent and a second solvent, wherein said first solvent is firstly added, followed by said second solvent, wherein said first solvent is water, and said second solvent is selected from methanol or halogenated fatty alcohol (particularly trifluoroethanol); or adding the solvent system comprising or consisting of a first solvent, a second solvent, and a third solvent, wherein said first solvent is firstly added, sequentially followed by said second solvent and said third solvent, wherein said first solvent is water, and a combination of said second solvent/said third solvent is alcohols/ketones, alcohols/ethers, esters/nitriles, ketones/esters, or nitriles/N,N-dimethylformamide.

Embodiment 2) relates to the method of Embodiment 1), wherein said alcohols are preferably selected from a group consisting of methanol, ethanol, n-propanol, isopropanol, n-butanol, sec-butanol, pentanol, and hexanol; said ketones are preferably selected from a group consisting of acetone, butanone, and 2-pentanone; said ethers are preferably selected from a group consisting of ethyl ether, isopropyl ether, methyl tert-butyl ether, tetrahydrofuran, or 1,4-dioxane; said esters are preferably selected from a group consisting of ethyl formate, propyl formate, isopropyl formate, methyl acetate, ethyl acetate, and isopropyl acetate; and said nitriles are preferably selected from a group consisting of acetonitrile, propionitrile, butyronitrile, and isobutyronitrile.

Embodiment 3) relates to the method of Embodiment 1), wherein the solvent system consisting of said first solvent and said second solvent is added to said compound, wherein said first solvent is firstly added, followed by said second solvent, wherein said first solvent is water, and said second solvent is selected from methanol or trifluoroethanol.

Embodiment 4) relates to the method of Embodiment 1), wherein the solvent system consisting of said first solvent, said second solvent and said third solvent is added to said compound, wherein said first solvent is firstly added, sequentially followed by said second solvent and said third solvent, wherein said first solvent is water, said second solvent is different from said third solvent, and a combination of said second solvent/said third solvent is ethanol/acetone, isopropanol/tetrahydrofuran, ethyl acetate/acetonitrile, n-propanol/1,4-dioxane, acetone/isopropyl acetate, or acetonitrile/N,N-dimethylformamide.

Embodiment 5) relates to the method of any one of Embodiments 1)-4), wherein said clear solution is allowed to stand at room temperature or at a crystallization temperature of about 40-60° C. (particularly about 40° C., about 50° C., or about 60° C.) until it volatizes to dryness to obtain said crystalline form.

Embodiment 6) relates to the method of any one of Embodiments 1)-4), wherein a mass-to-volume ratio of said compound to the total solvent is about 10 mg:0.05 ml-100 mg:250 ml (particularly, the mass-to-volume ratio may be, for example, about 100 mg:0.5 ml, 100 mg:0.6 ml-100 mg:250 ml, 100 mg:0.7 ml-100 mg:250 ml, 100 mg:0.8 ml-100 mg:250 ml, 100 mg:0.9 ml-100 mg:250 ml, 100 mg:1.0 ml-100 mg:250 ml, 100 mg:1.5 ml-100 mg:250 ml, 100 mg:2.0 ml-100 mg:250 ml, 100 mg:2.5 ml-100 mg:250ml, 100 mg:3.0 ml-100 mg:250 ml, 100 mg:3.5 ml-100 mg:250 ml, 100 mg:4.0 ml-100 mg:250 ml, 100 mg:4.5 ml-100 mg:250 ml, 100 mg:5.0 ml-100 mg:250 ml, 100 mg:5.5 ml-100 mg:250 ml, 100 mg:6.0 ml-100 mg:250 ml, 100 mg:6.5 ml-100 mg:250 ml, 100 mg:7.0 ml-100mg:250 ml, 100 mg:7.5 ml-100 mg:250 ml, 100 mg:8.0 ml-100 mg:250 ml, 100 mg:8.5 ml-100 mg:250 ml, 100 mg:9.0 ml-100 mg:250 ml, 100 mg:9.5 ml-100 mg:250 ml, 100 mg:10.0 ml-100 mg:250 ml, 100 mg:10.5 ml-100 mg:250 ml, 100 mg:11.0 ml-100 mg:250 ml, 100 mg:11.5 ml-100 mg:250 ml, 100 mg:12.0 ml-100 mg:250 ml, 100 mg:12.5 ml-100 mg:250 ml, 100 mg:13.0 ml-100 mg:250 ml, 100 mg:13.5 ml-100 mg:250 ml, 100 mg:14.0 ml-100 mg:250 ml, 100 mg:14.5 ml-100 mg:250 ml, 100 mg:15.0 ml-100 mg:250 ml, 100 mg:15.5 ml-100 mg:250 ml, 100 mg:16.0 ml-100 mg:250 ml, 100 mg:16.5 ml-100 mg:250 ml, 100 mg:17.0 ml-100 mg:250 ml, 100 mg:17.5 ml-100 mg:250 ml, 100 mg:18.0 ml-100 mg:250 ml, 100 mg:18.5 ml-100 mg:250 ml, 100 mg:19.0 ml-100 mg:250 ml, 100 mg:19.5 ml-100 mg:250 ml, 100 mg:20 ml-100 mg:250 ml, 100 mg:30 ml-100 mg:250 ml, 100 mg:35 ml-100 mg:250 ml, 100 mg:40 ml-100 mg:250 ml, 100 mg:45 ml-100 mg:250 ml, 100 mg:50 ml-100 mg:250 ml, 100 mg:55 ml-100 mg:250 ml, 100 mg:60 ml-100 mg:250 ml, 100 mg:65 ml-100 mg:250 ml, 100 mg:70 ml-100 mg:250 ml, 100 mg:75 ml-100 mg:250 ml, 100 mg:80 ml-100 mg:250 ml, 100 mg:85 ml-100 mg:250 ml, 100 mg:90 ml-100 mg:250 ml, 100 mg:95 ml-100 mg:250 ml, 100 mg:100 ml-100 mg:250 ml, 100 mg:105 ml-100 mg:250 ml, 100 mg:110 ml-100 mg:250 ml, 100 mg:120 ml-100 mg:250 ml, 100 mg:130 ml-100 mg:250 ml, 100 mg:140 ml-100 mg:250 ml, 100 mg:150 ml-100 mg:250 ml, 100 mg:160 ml-100 mg:250 ml, 100 mg:170 ml-100 mg:250 ml, 100 mg:180 ml-100 mg:250 ml, 100 mg:190 ml-100 mg:250 ml, 100 mg:200 ml-100 mg:250 ml, 100 mg:210 ml-100 mg:250 ml, 100 mg:220 ml-100 mg:250 ml, 100 mg:230 ml-100 mg:250 ml, 100 mg:240 ml-100 mg:250 ml, or 100 mg:250 ml). A volume of said total solvent is a volume of said first solvent when said solvent system consists of said first solvent; a volume of said total solvent is a sum of volumes of said first solvent and said second solvent when said solvent system consists of said first solvent and said second solvent; and by parity of reasoning, a volume of said total solvent is a sum of volumes of said first solvent, said second solvent, and said third solvent when said solvent system consists of said first solvent, said second solvent, and said third solvent.

Embodiment 7) relates to the method of Embodiment 3), wherein a volume ratio of said first solvent to said second solvent is about 1:0.01-1:200 (particularly, the volume ratio may be, for example, about 1:0.02-1:200, 1:0.03-1:200, 1:0.04-1:200, 1:0.05-1:200, 1:0.06-1:200, 1:0.07-1:200, 1:0.08-1:200, 1:0.09-1:200, 1:0.1-1:200, 1:0.15-1:200, 1:0.2-1:200, 1:0.25-1:200, 1:0.3-1:200, 1:0.35-1:200, 1:0.4-1:200, 1:0.45-1:200, 1:0.5-1:200, 1:0.55-1:200, 1:0.6-1:200, 1:0.65-1:200, 1:0.7-1:200, 1:0.75-1:200, 1:0.8-1:200, 1:0.85-1:200, 1:0.9-1:200, 1:0.95-1:200, 1:1-1:200, 1:1.5-1:200, 1:1.6-1:200, 1:1.7-1:200, 1:1.8-1:200, 1:1.9-1:200, 1:2-1:200, 1:3-1:200, 1:4-1:200, 1:5-1:200, 1:6-1:200, 1:7-1:200, 1:8-1:200, 1:9-1:200, 1:10-1:200, 1:11-1:200, 1:12-1:200, 1:13-1:200, 1:14-1:200, 1:15-1:200, 1:16-1:200, 1:17-1:200, 1:18-1:200, 1:19-1:200, 1:20-1:200, 1:21-1:200, 1:22-1:200, 1:23-1:200, 1:24-1:200, 1:25-1:200, 1:26-1:200, 1:27-1:200, 1:28-1:200, 1:29-1:200, 1:30-1:200, 1:35-1:200, 1:40-1:200, 1:45-1:200, 1:50-1:200, 1:55-1:200, 1:60-1:200, 1:65-1:200, 1:70-1:200, 1:75-1:200, 1:80-1:200, 1:85-1:200, 1:90-1:200, 1:95-1:200, 1:100-1:200, 1:110-1:200, 1:120-1:200, 1:130-1:200, 1:140-1:200, 1:150-1:200, 1:160-1:200, 1:170-1:200, 1:180-1:200, 1:190-1:200, or 1:200).

Embodiment 8) relates to the method of Embodiment 4), wherein a volume ratio of said first solvent to said second solvent to said third solvent is about 1:0.01-200:0.01-200 (particularly, the volume ratio may be, for example, about 1:1-1:200:200, 1:2:1-1:200:200, 1:1:2-1:200:200, 1:1:3-1:200:200, 1:0.02:0.02-1:200:200, 1:0.05:0.05-1:200:200, 1:0.1:0.1-1:200:200, 1:0.15:0.15-1:200:200, 1:0.2:0.2-1:200:200, 1:0.25:0.25-1:200:200, 1:0.3:0.3-1:200:200, 1:0.35:0.35-1:200:200, 1:0.4:0.4-1:200:200, 1:0.45:0.45-1:200:200, 1:0.5:0.5-1:200:200, 1:0.55:0.55-1:200:200, 1:0.6:0.6-1:200:200, 1:0.65:0.65-1:200:200, 1:0.7:0.7-1:200:200, 1:0.75:0.75-1:200:200, 1:0.8:0.8-1:200:200, 1:0.85:0.85-1:200:200, 1:0.9:0.9-1:200:200, 1:0.95:0.95-1:200:200, 1:1.5:1-1:200:200, 1:1.5:1.5-1:200:200, 1:1.6:1-1:200:200, 1:1.6:1.6-1:200:200, 1:1.7:1-1:200:200, 1:1.7:1.7-1:200:200, 1:1.8:1.8-1:200:200, 1:1.9:1.9-1:200:200, 1:2:2-1:200:200, 1:2:3-1:200:200, 1:3:1-1:200:200, 1:3:2-1:200:200, 1:3:3-1:200:200, 1:4:4-1:200:200, 1:4:1-1:200:200, 1:4:2-1:200:200, 1:4:3-1:200:200, 1:1:4-1:200:200, 1:2:4-1:200:200, 1:3:4-1:200:200, 1:5:5-1:200:200, 1:6:6-1:200:200, 1:7:7-1:200:200, 1:8:8-1:200:200, 1:9:9-1:200:200, 1:5:10-1:200:200, 1:10:10-1:200:200, 1:11:11-1:200:200, 1:12:12-1:200:200, 1:13:13-1:200:200, 1:14:14-1:200:200, 1:15:15-1:200:200, 1:16:16-1:200:200, 1:17:17-1:200:200, 1:18:18-1:200:200, 1:19:19-1:200:200, 1:20:20-1:200:200, 1:21:21-1:200:200, 1:22:22-1:200:200, 1:23:23-1:200:200, 1:24:24-1:200:200, 1:25:25-1:200:200, 1:26:26-1:200:200, 1:27:27-1:200:200, 1:28:28-1:200:200, 1:29:29-1:200:200, 1:30:30-1:200:200, 1:35:35-1:200:200, 1:40:40-1:200:200, 1:45:45-1:200:200, 1:50:50-1:200:200, 1:55:55-1:200:200, 1:60:60-1:200:200, 1:65:65-1:200:200, 1:70:70-1:200:200, 1:75:75-1:200:200, 1:80:80-1:200:200, 1:85:85-1:200:200, 1:90:90-1:200:200, 1:95:95-1:200:200, 1:100:100-1:200:200, 1:110:110-1:200:200, 1:120:120-1:200:200, 1:130:130-1:200:200, 1:140:140-1:200:200, 1:150:150-1:200:200, 1:160:160-1:200:200, 1:170:170-1:200:200, 1:180:180-1:200:200, 1:190:190-1:200:200, or 1:200:200).

Embodiment 9) relates to a method for preparing the Crystalline Form I of compound 3-((L-valyl)amino)-1-propanesulfonic acid, said method comprising the following steps: adding a solvent system to the compound 3-((L-valyl)amino)-1-propanesulfonic acid to obtain a suspension solution, and stirring to obtain said crystalline form, wherein the step of adding the solvent system comprises (or consists of):

adding the solvent system consisting of a first solvent, wherein said first solvent is selected from ethanol, isopropanol, propanol, water-saturated sec-butanol, or water-saturated esters solvent (particularly water-saturated ethyl acetate); or adding the solvent system consisting of a first solvent and a second solvent, wherein said first solvent is firstly added, followed by said second solvent, wherein said first solvent is different from said second solvent, and a combination of said first solvent/said second solvent is aromatics solvent/alcohols, alicyclic hydrocarbons solvent/alcohols, ethers/nitriles, alkanes solvent/halogenated alkanes solvent, or ethers/alcohols; or adding the solvent system comprising or consisting of a first solvent, a second solvent, and a third solvent, wherein said first solvent is firstly added, sequentially followed by said second solvent and said third solvent, wherein said third solvent is water, said first solvent is different from said second solvent, and a combination of said first solvent/said second solvent is alcohols/ketones, halogenated fatty alcohols/nitriles, alcohols/esters, ketones/nitriles, first ethers/second ethers, nitriles/nitromethane, alcohols/fatty acids, or ethers/esters.

Embodiment 10) relates to the method of Embodiment 9), wherein said aromatics solvent is preferably selected from a group consisting of toluene and ethylbenzene; said alcohols are preferably selected from a group consisting of methanol, ethanol, n-propanol, isopropanol, n-butanol, sec-butanol, pentanol, and hexanol; said alicyclic hydrocarbons solvent is preferably selected from a group consisting of cyclohexane and methylcyclohexane; said ethers are preferably selected from a group consisting of ethyl ether, isopropyl ether, methyl tert-butyl ether, tetrahydrofuran, or 1,4-dioxane; said nitriles are preferably selected from a group consisting of acetonitrile, propionitrile, butyronitrile, and isobutyronitrile; said alkanes solvent is preferably selected from a group consisting of n-hexane and n-heptane; said halogenated alkanes solvent is preferably selected from a group consisting of chloroform and dichloromethane; said ketones are preferably selected from a group consisting of acetone, butanone, and 2-pentanone; said esters are preferably selected from a group consisting of ethyl formate, propyl formate, isopropyl formate, methyl acetate, ethyl acetate, and isopropyl acetate; said halogenated fatty alcohols are preferably trifluoroethanol; and said fatty acids are preferably acetic acid.

Embodiment 11) relates to the method of Embodiment 9), wherein said first ethers and said second ethers differ and are each independently selected from a group consisting of ethyl ether, isopropyl ether, methyl tert-butyl ether, tetrahydrofuran, or 1,4-dioxane.

Embodiment 12) relates to the method of Embodiment 9), wherein said solvent system consisting of said first solvent and said second solvent is added to said compound, wherein said first solvent is firstly added, followed by said second solvent, wherein a combination of said first solvent/said second solvent is toluene/n-butanol, methylcyclohexane/isopropanol, isopropyl ether/acetonitrile, n-heptane/chloroform, or tetrahydrofuran/methanol.

Embodiment 13) relates to the method of Embodiment 9), wherein said solvent system consisting of said first solvent, said second solvent, and said third solvent is added to said compound, wherein said first solvent is firstly added, sequentially followed by said second solvent and said third solvent, wherein said third solvent is water, said first solvent differs from said second solvent, and a combination of said first solvent/said second solvent is methanol/acetone, trifluoroethanol/acetonitrile, n-propanol/isopropyl acetate, acetone/acetonitrile, tetrahydrofuran/methyl tert-butyl ether, acetonitrile/nitromethane, ethanol/butanone, n-butanol/acetic acid, or 1,4-dioxane/isopropyl acetate.

Embodiment 14) relates to the method of any one of Embodiments 9)-13), wherein said suspension solution is stirred to crystallize at a crystallization temperature of about 10-60° C. (preferably, about 10-40° C., about 20-50° C., and about 20-40° C.).

Embodiment 15) relates to the method of any one of Embodiments 9)-13), wherein a mass-to-volume ratio of said compound to the total solvent is about 10 mg:0.05 ml-100 mg:250 ml (particularly, the mass-to-volume ratio may be, for example, about 100 mg:0.5 ml, 100 mg:0.6 ml-100 mg:250 ml, 100 mg:0.7 ml-100 mg:250 ml, 100 mg:0.8 ml-100 mg:250 ml, 100 mg:0.9 ml-100 mg:250 ml, 100 mg:1.0 ml-100 mg:250 ml, 100 mg:1.5 ml-100 mg:250 ml, 100 mg:2.0 ml-100 mg:250 ml, 100 mg:2.5 ml-100 mg:250 ml, 100 mg:3.0 ml-100 mg:250 ml, 100 mg:3.5 ml-100 mg:250 ml, 100 mg:4.0 ml-100 mg:250 ml, 100 mg:4.5 ml-100 mg:250 ml, 100 mg:5.0 ml-100 mg:250 ml, 100 mg:5.5 ml-100 mg:250 ml, 100 mg:6.0 ml-100 mg:250 ml, 100 mg:6.5 ml-100 mg:250 ml, 100 mg:7.0 ml-100 mg:250 ml, 100 mg:7.5 ml-100 mg:250 ml, 100 mg:8.0 ml-100 mg:250 ml, 100 mg:8.5 ml-100 mg:250 ml, 100 mg:9.0 ml-100 mg:250 ml, 100 mg:9.5 ml-100 mg:250 ml, 100 mg:10.0 ml-100 mg:250 ml, 100 mg:10.5 ml-100 mg:250 ml, 100 mg:11.0 ml-100 mg:250 ml, 100 mg:11.5 ml-100 mg:250 ml, 100 mg:12.0 ml-100 mg:250 ml, 100 mg:12.5 ml-100 mg:250 ml, 100 mg:13.0 ml-100 mg:250 ml, 100 mg:13.5 ml-100 mg:250 ml, 100 mg:14.0 ml-100 mg:250 ml, 100 mg:14.5 ml-100 mg:250 ml, 100 mg:15.0 ml-100 mg:250 ml, 100 mg:15.5 ml-100 mg:250 ml, 100 mg:16.0 ml-100 mg:250 ml, 100 mg:16.5 ml-100 mg:250 ml, 100 mg:17.0 ml-100 mg:250 ml, 100 mg:17.5 ml-100 mg:250 ml, 100 mg:18.0 ml-100mg:250 ml, 100 mg:18.5 ml-100 mg:250 ml, 100 mg:19.0 ml-100 mg:250 ml, 100 mg:19.5 ml-100 mg:250 ml, 100 mg:20 ml-100 mg:250 ml, 100 mg:30 ml-100 mg:250 ml, 100 mg:35 ml-100 mg:250 ml, 100 mg:40 ml-100 mg:250 ml, 100 mg:45 ml-100 mg:250 ml, 100 mg:50 ml-100 mg:250 ml, 100 mg:55 ml-100 mg:250 ml, 100 mg:60 ml-100 mg:250 ml, 100 mg:65 ml-100 mg:250 ml, 100 mg:70 ml-100 mg:250 ml, 100 mg:75 ml-100 mg:250 ml, 100 mg:80 ml-100 mg:250 ml, 100 mg:85 ml-100 mg:250 ml, 100 mg:90 ml-100 mg:250 ml, 100 mg:95 ml-100 mg:250 ml, 100 mg:100 ml-100 mg:250 ml, 100 mg:105 ml-100 mg:250 ml, 100 mg:110 ml-100 mg:250 ml, 100 mg:120 ml-100 mg:250 ml, 100 mg:130 ml-100 mg:250 ml, 100 mg:140 ml-100 mg:250 ml, 100 mg:150 ml-100 mg:250 ml, 100 mg:160 ml-100 mg:250 ml, 100 mg:170 ml-100 mg:250 ml, 100mg:180 ml-100 mg:250 ml, 100 mg:190 ml-100 mg:250 ml, 100 mg:200 ml-100 mg:250 ml, 100 mg:210 ml-100 mg:250 ml, 100 mg:220 ml-100 mg:250 ml, 100 mg:230 ml-100 mg:250 ml, 100 mg:240 ml-100 mg:250 ml, or 100 mg:250 ml). A volume of said total solvent is a volume of said first solvent when said solvent system consists of said first solvent; a volume of said total solvent is a sum of volumes of said first solvent and said second solvent when said solvent system consists of said first solvent and said second solvent; and by parity of reasoning, a volume of said total solvent is a sum of volumes of said first solvent, said second solvent, and said third solvent when said solvent system consists of said first solvent, said second solvent, and said third solvent.

Embodiment 16) relates to the method of Embodiment 12), wherein a volume ratio of said first solvent to said second solvent is about 1:0.01-1:200 (particularly, the volume ratio may be, for example, about 1:0.02-1:200, 1:0.03-1:200, 1:0.04-1:200, 1:0.05-1:200, 1:0.06-1:200, 1:0.07-1:200, 1:0.08-1:200, 1:0.09-1:200, 1:0.1-1:200, 1:0.15-1:200, 1:0.2-1:200, 1:0.25-1:200, 1:0.3-1:200, 1:0.35-1:200, 1:0.4-1:200, 1:0.45-1:200, 1:0.5-1:200, 1:0.55-1:200, 1:0.6-1:200, 1:0.65-1:200, 1:0.7-1:200, 1:0.75-1:200, 1:0.8-1:200, 1:0.85-1:200, 1:0.9-1:200, 1:0.95-1:200, 1:1-1:200, 1:1.5-1:200, 1:1.6-1:200, 1:1.7-1:200, 1:1.8-1:200, 1:1.9-1:200, 1:2-1:200, 1:3-1:200, 1:4-1:200, 1:5-1:200, 1:6-1:200, 1:7-1:200, 1:8-1:200, 1:9-1:200, 1:10-1:200, 1:11-1:200, 1:12-1:200, 1:13-1:200, 1:14-1:200, 1:15-1:200, 1:16-1:200, 1:17-1:200, 1:18-1:200, 1:19-1:200, 1:20-1:200, 1:21-1:200, 1:22-1:200, 1:23-1:200, 1:24-1:200, 1:25-1:200, 1:26-1:200, 1:27-1:200, 1:28-1:200, 1:29-1:200, 1:30-1:200, 1:35-1:200, 1:40-1:200, 1:45-1:200, 1:50-1:200, 1:55-1:200, 1:60-1:200, 1:65-1:200, 1:70-1:200, 1:75-1:200, 1:80-1:200, 1:85-1:200, 1:90-1:200, 1:95-1:200, 1:100-1:200, 1:110-1:200, 1:120-1:200, 1:130-1:200, 1:140-1:200, 1:150-1:200, 1:160-1:200, 1:170-1:200, 1:180-1:200, 1:190-1:200, or 1:200).

Embodiment 17) relates to the method of Embodiment 13), wherein a volume ratio of said first solvent to said second solvent to said third solvent is about 1:0.01-200:0.01-200 (particularly, the volume ratio may be, for example, about 1:1:1-1:200:200, 1:2:1-1:200:200, 1:1:2-1:200:200, 1:1:3-1:200:200, 1:0.02:0.02-1:200:200, 1:0.05:0.05-1:200:200, 1:0.1:0.1-1:200:200, 1:0.15:0.15-1:200:200, 1:0.2:0.2-1:200:200, 1:0.25:0.25-1:200:200, 1:0.3:0.3-1:200:200, 1:0.35:0.35-1:200:200, 1:0.4:0.4-1:200:200, 1:0.45:0.45-1:200:200, 1:0.5:0.5-1:200:200, 1:0.55:0.55-1:200:200, 1:0.6:0.6-1:200:200, 1:0.65:0.65-1:200:200, 1:0.7:0.7-1:200:200, 1:0.75:0.75-1:200:200, 1:0.8:0.8-1:200:200, 1:0.85:0.85-1:200:200, 1:0.9:0.9-1:200:200, 1:0.95:0.95-1:200:200, 1:1.5:1-1:200:200, 1:1.5:1.5-1:200:200, 1:1.6:1-1:200:200, 1:1.6:1.6-1:200:200, 1:1.7:1-1:200:200, 1:1.7:1.7-1:200:200, 1:1.8:1.8-1:200:200, 1:1.9:1.9-1:200:200, 1:2:2-1:200:200, 1:2:3-1:200:200, 1:3:1-1:200:200, 1:3:2-1:200:200, 1:3:3-1:200:200, 1:4:4-1:200:200, 1:4:1-1:200:200, 1:4:2-1:200:200, 1:4:3-1:200:200, 1:1:4-1:200:200, 1:2:4-1:200:200, 1:3:4-1:200:200, 1:5:5-1:200:200, 1:6:6-1:200:200, 1:7:7-1:200:200, 1:8:8-1:200:200, 1:9:9-1:200:200, 1:5:10-1:200:200, 1:10:10-1:200:200, 1:11:11-1:200:200, 1:12:12-1:200:200, 1:13:13-1:200:200, 1:14:14-1:200:200, 1:15:15-1:200:200, 1:16:16-1:200:200, 1:17:17-1:200:200, 1:18:18-1:200:200, 1:19:19-1:200:200, 1:20:20-1:200:200, 1:21:21-1:200:200, 1:22:22-1:200:200, 1:23:23-1:200:200, 1:24:24-1:200:200, 1:25:25-1:200:200, 1:26:26-1:200:200, 1:27:27-1:200:200, 1:28:28-1:200:200, 1:29:29-1:200:200, 1:30:30-1:200:200, 1:35:35-1:200:200, 1:40:40-1:200:200, 1:45:45-1:200:200, 1:50:50-1:200:200, 1:55:55-1:200:200, 1:60:60-1:200:200, 1:65:65-1:200:200, 1:70:70-1:200:200, 1:75:75-1:200:200, 1:80:80-1:200:200, 1:85:85-1:200:200, 1:90:90-1:200:200, 1:95:95-1:200:200, 1:100:100-1:200:200, 1:110:110-1:200:200, 1:120:120-1:200:200, 1:130:130-1:200:200, 1:140:140-1:200:200, 1:150:150-1:200:200, 1:160:160-1:200:200, 1:170:170-1:200:200, 1:180:180-1:200:200, 1:190:190-1:200:200, or 1:200:200).

Embodiment 18) relates to a method for preparing the Crystalline Form I of compound 3-((L-valyl)amino)-1-propanesulfonic acid, said method comprising the following steps: sequentially adding a first solvent and a second solvent to the compound 3-((L-valyl)amino)-1-propanesulfonic acid to obtain a clear solution, adding a third solvent during stirring, and crystallizing to obtain said Crystalline Form I, wherein a combination of said first solvent/said second solvent/said third solvent is alcohols/water/ketones, halogenated fatty alcohols/water/nitriles, ketones/water/alcohols, ethers/water/alcohols, alcohols/water/N,N-dimethylformamide, alcohols/water/ethers, first alcohols/water/second alcohols, or nitriles/water/fatty acids, wherein said first alcohols differ from said second alcohols.

Embodiment 19) relates to the method of Embodiment 18), wherein said alcohols are preferably selected from a group consisting of methanol, ethanol, n-propanol, isopropanol, n-butanol, sec-butanol, pentanol, and hexanol; said ketones are preferably selected from a group consisting of acetone, butanone, and 2-pentanone; said halogenated fatty alcohols are preferably trifluoroethanol; said nitriles are preferably selected from a group consisting of acetonitrile, propionitrile, butyronitrile, and isobutyronitrile; said ethers are preferably selected from a group consisting of ethyl ether, isopropyl ether, methyl tert-butyl ether, tetrahydrofuran, or 1,4-dioxane; and said fatty acids are preferably acetic acid.

Embodiment 20) relates to the method of Embodiment 18), wherein a combination of said first solvent/said second solvent/said third solvent is methanol/water/acetone, trifluoroethanol/water/acetonitrile, n-propanol/water/tetrahydrofuran, acetone/water/isopropanol, tetrahydrofuran/water/n-butanol, ethanol/water/N,N-dimethylformamide, isopropanol/water/1,4-dioxane, n-butanol/water/methanol, 1,4-dioxane/water/ethanol, or acetonitrile/water/acetic acid.

Embodiment 21) relates to the method of any one of Embodiments 18)-20), wherein a mass-to-volume ratio of said compound to the total solvent is about 10 mg:0.05 ml-100 mg:250 ml (particularly, the mass-to-volume ratio may be, for example, about 100 mg:0.5 ml, 100 mg:0.6 ml-100 mg:250 ml, 100mg:0.7 ml-100mg:250 ml, 100 mg:0.8 ml-100 mg:250 ml, 100 mg:0.9 ml-100 mg:250 ml, 100 mg:1.0 ml-100 mg:250 ml, 100 mg:1.5 ml-100 mg:250 ml, 100 mg:2.0 ml-100 mg:250 ml, 100 mg:2.5 ml-100 mg:250 ml, 100 mg:3.0 ml-100 mg:250 ml, 100 mg:3.5 ml-100 mg:250 ml, 100 mg:4.0 ml-100 mg:250 ml, 100 mg:4.5 ml-100 mg:250 ml, 100 mg:5.0 ml-100 mg:250 ml, 100 mg:5.5 ml-100 mg:250 ml, 100 mg:6.0 ml-100 mg:250 ml, 100 mg:6.5 ml-100 mg:250 ml, 100 mg:7.0 ml-100 mg:250 ml, 100 mg:7.5 ml-100 mg:250 ml, 100 mg:8.0 ml-100 mg:250 ml, 100 mg:8.5 ml-100 mg:250 ml, 100 mg:9.0 ml-100 mg:250 ml, 100 mg:9.5 ml-100 mg:250 ml, 100 mg:10.0 ml-100 mg:250 ml, 100 mg:10.5 ml-100 mg:250 ml, 100 mg:11.0 ml-100 mg:250 ml, 100 mg:11.5 ml-100 mg:250 ml, 100 mg:12.0 ml-100 mg:250 ml, 100 mg:12.5 ml-100 mg:250 ml, 100 mg:13.0 ml-100 mg:250 ml, 100 mg:13.5 ml-100 mg:250 ml, 100 mg:14.0 ml-100 mg:250 ml, 100 mg:14.5 ml-100 mg:250 ml, 100 mg:15.0 ml-100 mg:250 ml, 100 mg:15.5 ml-100 mg:250 ml, 100 mg:16.0 ml-100 mg:250 ml, 100 mg:16.5 ml-100 mg:250 ml, 100 mg:17.0 ml-100 mg:250 ml, 100 mg:17.5 ml-100 mg:250 ml, 100 mg:18.0 ml-100 mg:250 ml, 100 mg:18.5 ml-100 mg:250 ml, 100 mg:19.0 ml-100 mg:250 ml, 100 mg:19.5 ml-100 mg:250ml, 100 mg:20 ml-100 mg:250 ml, 100 mg:30 ml-100 mg:250 ml, 100 mg:35 ml-100 mg:250 ml, 100 mg:40 ml-100 mg:250 ml, 100 mg:45 ml-100 mg:250 ml, 100 mg:50 ml-100 mg:250 ml, 100 mg:55 ml-100 mg:250 ml, 100 mg:60 ml-100 mg:250 ml, 100 mg:65 ml-100 mg:250 ml, 100 mg:70 ml-100 mg:250 ml, 100 mg:75 ml-100 mg:250 ml, 100 mg:80 ml-100 mg:250 ml, 100 mg:85 ml-100 mg:250 ml, 100 mg:90 ml-100 mg:250 ml, 100 mg:95 ml-100 mg:250 ml, 100 mg:100 ml-100 mg:250 ml, 100 mg:105 ml-100 mg:250 ml, 100 mg:110 ml-100 mg:250 ml, 100 mg:120 ml-100 mg:250 ml, 100 mg:130 ml-100 mg:250 ml, 100 mg:140 ml-100 mg:250 ml, 100 mg:150 ml-100 mg:250 ml, 100 mg:160 ml-100 mg:250 ml, 100 mg:170 ml-100 mg:250 ml, 100 mg:180 ml-100 mg:250 ml, 100 mg:190 ml-100 mg:250 ml, 100 mg:200 ml-100 mg:250 ml, 100 mg:210 ml-100 mg:250 ml, 100 mg:220 ml-100 mg:250 ml, 100 mg:230 ml-100 mg:250 ml, 100 mg:240 ml-100 mg:250 ml, or 100 mg:250 ml). A volume of the total solvent is a sum of volumes of said first solvent, said second solvent, and said third solvent when said solvent system consists of said first solvent, said second solvent, and said third solvent.

Embodiment 22) relates to the method of any one of Embodiments 18)-21), wherein a volume ratio of said first solvent to said second solvent to said third solvent is about 1:0.01-200:0.01-200 (particularly, the volume ratio may be, for example, about 1:1:1-1:200:200, 1:2:1-1:200:200, 1:1:2-1:200:200, 1:1:3-1:200:200, 1:0.02:0.02-1:200:200, 1:0.05:0.05-1:200:200, 1:0.1:0.1-1:200:200, 1:0.15:0.15-1:200:200, 1:0.2:0.2-1:200:200, 1:0.25:0.25-1:200:200, 1:0.3:0.3-1:200:200, 1:0.35:0.35-1:200:200, 1:0.4:0.4-1:200:200, 1:0.45:0.45-1:200:200, 1:0.5:0.5-1:200:200, 1:0.55:0.55-1:200:200, 1:0.6:0.6-1:200:200, 1:0.65:0.65-1:200:200, 1:0.7:0.7-1:200:200, 1:0.75:0.75-1:200:200, 1:0.8:0.8-1:200:200, 1:0.85:0.85-1:200:200, 1:0.9:0.9-1:200:200, 1:0.95:0.95-1:200:200, 1:1:5:1-1:200:200, 1:1:5:1.5-1:200:200, 1:1.6:1-1:200:200, 1:1.6:1.6-1:200:200, 1:1.7:1-1:200:200, 1:1.7:1.7-1:200:200, 1:1.8:1.8-1:200:200, 1:1.9:1.9-1:200:200, 1:2:2-1:200:200, 1:2:3-1:200:200, 1:3:1-1:200:200, 1:3:2-1:200:200, 1:3:3-1:200:200, 1:4:4-1:200:200, 1:4:1-1:200:200, 1:4:2-1:200:200, 1:4:3-1:200:200, 1:1:4-1:200:200, 1:2:4-1:200:200, 1:3:4-1:200:200, 1:5:5-1:200:200, 1:6:6-1:200:200, 1:7:7-1:200:200, 1:8:8-1:200:200, 1:9:9-1:200:200, 1:5:10-1:200:200, 1:10:10-1:200:200, 1:11:11-1:200:200, 1:12:12-1:200:200, 1:13:13-1:200:200, 1:14:14-1:200:200, 1:15:15-1:200:200, 1:16:16-1:200:200, 1:17:17-1:200:200, 1:18:18-1:200:200, 1:19:19-1:200:200, 1:20:20-1:200:200, 1:21:21-1:200:200, 1:22:22-1:200:200, 1:23:23-1:200:200, 1:24:24-1:200:200, 1:25:25-1:200:200, 1:26:26-1:200:200, 1:27:27-1:200:200, 1:28:28-1:200:200, 1:29:29-1:200:200, 1:30:30-1:200:200, 1:35:35-1:200:200, 1:40:40-1:200:200, 1:45:45-1:200:200, 1:50:50-1:200:200, 1:55:55-1:200:200, 1:60:60-1:200:200, 1:65:65-1:200:200, 1:70:70-1:200:200, 1:75:75-1:200:200, 1:80:80-1:200:200, 1:85:85-1:200:200, 1:90:90-1:200:200, 1:95:95-1:200:200, 1:100:100-1:200:200, 1:110:110-1:200:200, 1:120:120-1:200:200, 1:130:130-1:200:200, 1:140:140-1:200:200, 1:150:150-1:200:200, 1:160:160-1:200:200, 1:170:170-1:200:200, 1:180:180-1:200:200, 1:190:190-1:200:200, or 1:200:200).

Embodiment 23) relates to a method for preparing the Crystalline Form I of compound 3-((L-valyl)amino)-1-propanesulfonic acid, said method comprising the following steps: adding a solvent to the compound 3-((L-valyl)amino)-1-propanesulfonic acid at a temperature of about 30-80° C. (particularly, the temperature may be, for example, about 35-80° C., about 40-80° C., about 45-80° C., about 50-80° C., about 55-80° C., about 60-80° C., about 65-80° C., or about 70-80° C.) to obtain a clear solution, cooling, and crystallizing (for example, cooling is performed at a temperature lower than a heating temperature, e.g., about --20° C.-55° C., about −20° C.-50° C., about −20° C.-45° C., about −20° C.-40° C., about −20° C.-35° C., about −20° C.-30° C., about −20° C.-25° C., about −20° C.-20° C., about −20° C.-15° C., about −20° C.-10° C., about −20° C.-5° C., about −20° C.-0° C., about −20° C. to −5° C., about −20° C. to −10° C., or about −20° C. to −15° C.) to obtain said crystalline form, wherein the step of adding said solvent comprises (or consists of): firstly adding a first solvent, followed by sequentially adding a second solvent and a third solvent, wherein said first solvent is water or dimethyl sulfoxide, and a combination of said second solvent/said third solvent is alcohols/nitriles, alcohols/ethers, halogenated fatty acids/ketones, ketones/esters, halogenated alkanes/alcohols, ketones/aromatics, or nitriles/esters.

Embodiment 24) relates to the method of Embodiment 23), wherein said alcohols are selected from a group consisting of methanol, ethanol, n-propanol, isopropanol, n-butanol, sec-butanol, pentanol, and hexanol; said nitriles are selected from a group consisting of acetonitrile, propionitrile, butyronitrile, and isobutyronitrile; said ethers are selected from a group consisting of ethyl ether, isopropyl ether, methyl tert-butyl ether, tetrahydrofuran, or 1,4-dioxane; said halogenated fatty alcohols are trifluoroethanol; said ketones are selected from a group consisting of acetone, butanone, and 2-pentanone; said esters are selected from a group consisting of ethyl formate, propyl formate, isopropyl formate, methyl acetate, ethyl acetate, and isopropyl acetate; said halogenated alkanes solvent is selected from a group consisting of chloroform and dichloromethane; and said aromatics solvent is selected from a group consisting of toluene and ethylbenzene.

Embodiment 25) relates to the method of Embodiment 23) or 24), wherein a combination of said second solvent/said third solvent is methanol/acetonitrile, ethanol/1,4-dioxane, trifluoroethanol/acetone, isopropanol/tetrahydrofuran, acetone/ethyl acetate, chloroform/n-butanol, butanone/toluene, or acetonitrile/isopropyl acetate.

Embodiment 26) relates to the method of any one of Embodiments 23)-25), wherein a mass-to-volume ratio of said compound to the total solvent is about 10 mg:0.05 ml-100 mg:250 ml (particularly, the mass-to-volume ratio may be, for example, about 100 mg:0.5 ml, 100 mg:0.6 ml-100 mg:250 ml, 100 mg:0.7 ml-100 mg:250 ml, 100 mg:0.8 ml-100 mg:250 ml, 100 mg:0.9 ml-100 mg:250 ml, 100 mg:1.0 ml-100 mg:250 ml, 100 mg:1.5 ml-100 mg:250 ml, 100 mg:2.0 ml-100 mg:250 ml, 100 mg:2.5 ml-100 mg:250 ml, 100 mg:3.0 ml-100 mg:250 ml, 100 mg:3.5 ml-100 mg:250 ml, 100 mg:4.0 ml-100 mg:250 ml, 100 mg:4.5 ml-100 mg:250 ml, 100 mg:5.0 ml-100 mg:250 ml, 100 mg:5.5 ml-100 mg:250 ml, 100 mg:6.0 ml-100 mg:250 ml, 100 mg:6.5 ml-100 mg:250 ml, 100 mg:7.0 ml-100 mg:250 ml, 100 mg:7.5 ml-100 mg:250 ml, 100 mg:8.0 ml-100 mg:250 ml, 100 mg:8.5 ml-100 mg:250 ml, 100 mg:9.0 ml-100 mg:250 ml, 100 mg:9.5 ml-100 mg:250 ml, 100 mg:10.0 ml-100 mg:250 ml, 100 mg:10.5 ml-100 mg:250 ml, 100 mg:11.0 ml-100 mg:250 ml, 100 mg:11.5 ml-100 mg:250 ml, 100 mg:12.0 ml-100 mg:250 ml, 100 mg:12.5 ml-100 mg:250 ml, 100 mg:13.0 ml-100 mg:250 ml, 100 mg:13.5 ml-100 mg:250 ml, 100 mg:14.0 ml-100 mg:250 ml, 100 mg:14.5 ml-100 mg:250 ml, 100 mg:15.0 ml-100 mg:250 ml, 100 mg:15.5 ml-100 mg:250 ml, 100 mg:16.0 ml-100 mg:250 ml, 100 mg:16.5 ml-100 mg:250 ml, 100 mg:17.0 ml-100 mg:250 ml, 100 mg:17.5 ml-100 mg:250 ml, 100 mg:18.0 ml-100 mg:250 ml, 100 mg:18.5 ml-100 mg:250 ml, 100 mg:19.0 ml-100 mg:250 ml, 100 mg:19.5 ml-100 mg:250 ml, 100 mg:20 ml-100 mg:250 ml, 100 mg:30 ml-100 mg:250 ml, 100 mg:35 ml-100 mg:250 ml, 100 mg:40 ml-100 mg:250 ml, 100 mg:45 ml-100 mg:250 ml, 100 mg:50 ml-100 mg:250 ml, 100 mg:55 ml-100 mg:250 ml, 100 mg:60 ml-100 mg:250 ml, 100 mg:65 ml-100 mg:250 ml, 100 mg:70 ml-100 mg:250 ml, 100 mg:75 ml-100 mg:250 ml, 100 mg:80 ml-100 mg:250 ml, 100 mg:85 ml-100 mg:250 ml, 100 mg:90 ml-100 mg:250 ml, 100 mg:95 ml-100 mg:250 ml, 100 mg:100 ml-100 mg:250 ml, 100 mg:105 ml-100 mg:250 ml, 100 mg:110 ml-100 mg:250 ml, 100 mg:120 ml-100 mg:250 ml, 100 mg:130 ml-100 mg:250 ml, 100 mg:140 ml-100 mg:250 ml, 100 mg:150 ml-100 mg:250 ml, 100 mg:160 ml-100 mg:250 ml, 100 mg:170 ml-100 mg:250 ml, 100 mg:180 ml-100 mg:250 ml, 100 mg:190 ml-100 mg:250 ml, 100 mg:200 ml-100 mg:250 ml, 100 mg:210 ml-100 mg:250 ml, 100 mg:220 ml-100 mg:250 ml, 100 mg:230 ml-100 mg:250 ml, 100 mg:240 ml-100 mg:250 ml, or 100 mg:250 ml). A volume of said total solvent is a sum of volumes of said first solvent, said second solvent, and said third solvent when solvents are said first solvent, said second solvent, and said third solvent.

Embodiment 27) relates to the method of any one of Embodiments 23)-26), wherein a volume ratio of said first solvent to said second solvent to said third solvent is about 1:0.01-200:0.01-200 (particularly, the volume ratio may be, for example, about 1:1:1-1:200:200, 1:2:1-1:200:200, 1:1:2-1:200:200, 1:1:3-1:200:200, 1:0.02:0.02-1:200:200, 1:0.05:0.05-1:200:200, 1:0.1:0.1-1:200:200, 1:0.15:0.15-1:200:200, 1:0.2:0.2-1:200:200, 1:0.25:0.25-1:200:200, 1:0.3:0.3-1:200:200, 1:0.35:0.35-1:200:200, 1:0.4:0.4-1:200:200, 1:0.45:0.45-1:200:200, 1:0.5:0.5-1:200:200, 1:0.55:0.55-1:200:200, 1:0.6:0.6-1:200:200, 1:0.65:0.65-1:200:200, 1:0.7:0.7-1:200:200, 1:0.75:0.75-1:200:200, 1:0.8:0.8-1:200:200, 1:0.85:0.85-1:200:200, 1:0.9:0.9-1:200:200, 1:0.95:0.95-1:200:200, 1:1.5:1-1:200:200, 1:1.5:1.5-1:200:200, 1:1.6:1-1:200:200, 1:1.6:1.6-1:200:200, 1:1.7:1-1:200:200, 1:1.7:1.7-1:200:200, 1:1.8:1.8-1:200:200, 1:1.9:1.9-1:200:200, 1:2:2-1:200:200, 1:2:3-1:200:200, 1:3:1-1:200:200, 1:3:2-1:200:200, 1:3:3-1:200:200, 1:4:4-1:200:200, 1:4:1-1:200:200, 1:4:2-1:200:200, 1:4:3-1:200:200, 1:1:4-1:200:200, 1:2:4-1:200:200, 1:3:4-1:200:200, 1:5:5-1:200:200, 1:6:6-1:200:200, 1:7:7-1:200:200, 1:8:8-1:200:200, 1:9:9-1:200:200, 1:5:10-1:200:200, 1:10:10-1:200:200, 1:11:11-1:200:200, 1:12:12-1:200:200, 1:13:13-1:200:200, 1:14:14-1:200:200, 1:15:15-1:200:200, 1:16:16-1:200:200, 1:17:17-1:200:200, 1:18:18-1:200:200, 1:19:19-1:200:200, 1:20:20-1:200:200, 1:21:21-1:200:200, 1:22:22-1:200:200, 1:23:23-1:200:200, 1:24:24-1:200:200, 1:25:25-1:200:200, 1:26:26-1:200:200, 1:27:27-1:200:200, 1:28:28-1:200:200, 1:29:29-1:200:200, 1:30:30-1:200:200, 1:35:35-1:200:200, 1:40:40-1:200:200, 1:45:45-1:200:200, 1:50:50-1:200:200, 1:55:55-1:200:200, 1:60:60-1:200:200, 1:65:65-1:200:200, 1:70:70-1:200:200, 1:75:75-1:200:200, 1:80:80-1:200:200, 1:85:85-1:200:200, 1:90:90-1:200:200, 1:95:95-1:200:200, 1:100:100-1:200:200, 1:110:110-1:200:200, 1:120:120-1:200:200, 1:130:130-1:200:200, 1:140:140-1:200:200, 1:150:150-1:200:200, 1:160:160-1:200:200, 1:170:170-1:200:200, 1:180:180-1:200:200, 1:190:190-1:200:200, or 1:200:200).

Embodiment 28) relates to a method for preparing the Crystalline Form I of compound 3-((L-valyl)amino)-1-propanesulfonic acid, said method comprising the following steps: adding a first solvent to the compound 3-((L-valyl)amino)-1-propanesulfonic acid to obtain a clear solution, then placing it into a solvent atmosphere of a second solvent for standing, and crystallizing to obtain said crystalline form, wherein said first solvent is water, and said second solvent is ethers (particularly, ethyl ether, isopropyl ether, methyl tert-butyl ether, tetrahydrofuran, or 1,4-dioxane).

Embodiment 29) relates to the method of Embodiment 28), wherein a mass-to-volume ratio of said compound to the total solvent is about 10 mg:0.01 ml-100 mg:250 ml (particularly, the mass-to-volume ratio may be, for example, about 100 mg:0.1 ml, 100 mg:0.5 ml, 100 mg:0.6 ml-100 mg:250 ml, 100 mg:0.7 ml-100 mg:250 ml, 100 mg:0.8 ml-100 mg:250 ml, 100 mg:0.9 ml-100 mg:250 ml, 100 mg:1.0 ml-100 mg:250 ml, 100 mg:1.5 ml-100 mg:250 ml, 100 mg:2.0 ml-100 mg:250 ml, 100 mg:2.5 ml-100 mg:250 ml, 100 mg:3.0 ml-100 mg:250 ml, 100 mg:3.5 ml-100 mg:250 ml, 100 mg:4.0 ml-100 mg:250 ml, 100 mg:4.5 ml-100 mg:250 ml, 100 mg:5.0 ml-100 mg:250 ml, 100 mg:5.5 ml-100 mg:250 ml, 100 mg:6.0 ml-100 mg:250 ml, 100 mg:6.5 ml-100 mg:250 ml, 100 mg:7.0 ml-100 mg:250 ml, 100 mg:7.5 ml-100 mg:250 ml, 100 mg:8.0 ml-100 mg:250 ml, 100 mg:8.5 ml-100 mg:250 ml, 100 mg:9.0 ml-100 mg:250 ml, 100 mg:9.5 ml-100 mg:250 ml, 100 mg:10.0 ml-100 mg:250 ml, 100 mg:10.5 ml-100 mg:250 ml, 100 mg:11.0 ml-100 mg:250 ml, 100 mg:11.5 ml-100 mg:250 ml, 100 mg:12.0 ml-100 mg:250 ml, 100 mg:12.5 ml-100 mg:250 ml, 100 mg:13.0 ml-100 mg:250 ml, 100 mg:13.5 ml-100 mg:250 ml, 100 mg:14.0 ml-100 mg:250 ml, 100 mg:14.5 ml-100 mg:250 ml, 100 mg:15.0 ml-100 mg:250 ml, 100 mg:15.5 ml-100 mg:250 ml, 100 mg:16.0 ml-100 mg:250 ml, 100 mg:16.5 ml-100 mg:250 ml, 100 mg:17.0 ml-100 mg:250 ml, 100 mg:17.5 ml-100 mg:250 ml, 100 mg:18.0 ml-100 mg:250 ml, 100 mg:18.5 ml-100 mg:250 ml, 100 mg:19.0 ml-100 mg:250 ml, 100 mg:19.5 ml-100 mg:250 ml, 100 mg:20 ml-100 mg:250 ml, 100 mg:30 ml-100 mg:250 ml, 100 mg:35 ml-100 mg:250 ml, 100 mg:40 ml-100 mg:250 ml, 100 mg:45 ml-100 mg:250 ml, 100 mg:50 ml-100 mg:250 ml, 100 mg:55 ml-100 mg:250 ml, 100 mg:60 ml-100 mg:250 ml, 100 mg:65 ml-100 mg:250 ml, 100 mg:70 ml-100 mg:250 ml, 100 mg:75 ml-100 mg:250 ml, 100 mg:80 ml-100 mg:250 ml, 100 mg:85 ml-100 mg:250 ml, 100 mg:90 ml-100 mg:250 ml, 100 mg:95 ml-100 mg:250 ml, 100 mg:100 ml-100 mg:250 ml, 100 mg:105 ml-100 mg:250 ml, 100 mg:110 ml-100 mg:250 ml, 100 mg:120 ml-100 mg:250 ml, 100 mg:130 ml-100 mg:250 ml, 100 mg:140 ml-100 mg:250 ml, 100 mg:150 ml-100 mg:250 ml, 100 mg:160 ml-100 mg:250 ml, 100 mg:170 ml-100 mg:250 ml, 100 mg:180 ml-100 mg:250 ml, 100 mg:190 ml-100 mg:250 ml, 100 mg:200 ml-100 mg:250 ml, 100 mg:210 ml-100 mg:250 ml, 100 mg:220 ml-100 mg:250 ml, 100 mg:230 ml-100 mg:250 ml, 100 mg:240 ml-100 mg:250 ml, or 100 mg:250 ml). A volume of said total solvent is a sum of volumes of said first solvent and said second solvent when solvents are said first solvent and said second solvent.

Embodiment 30) relates to the method of Embodiment 28) or 29), wherein a volume ratio of said first solvent to said second solvent is about 1:0.01-1:200 (particularly, the volume ratio, for example, about 1:0.02-1:200, 1:0.03-1:200, 1:0.04-1:200, 1:0.05-1:200, 1:0.06-1:200, 1:0.07-1:200, 1:0.08-1:200, 1:0.09-1:200, 1:0.1-1:200, 1:0.15-1:200, 1:0.2-1:200, 1:0.25-1:200, 1:0.3-1:200, 1:0.35-1:200, 1:0.4-1:200, 1:0.45-1:200, 1:0.5-1:200, 1:0.55-1:200, 1:0.6-1:200, 1:0.65-1:200, 1:0.7-1:200, 1:0.75-1:200, 1:0.8-1:200, 1:0.85-1:200, 1:0.9-1:200, 1:0.95-1:200, 1:1-1:200, 1:1.5-1:200, 1:1.6-1:200, 1:1.7-1:200, 1:1.8-1:200, 1:1.9-1:200, 1:2-1:200, 1:3-1:200, 1:4-1:200, 1:5-1:200, 1:6-1:200, 1:7-1:200, 1:8-1:200, 1:9-1:200, 1:10-1:200, 1:11-1:200, 1:12-1:200, 1:13-1:200, 1:14-1:200, 1:15-1:200, 1:16-1:200, 1:17-1:200, 1:18-1:200, 1:19-1:200, 1:20-1:200, 1:21-1:200, 1:22-1:200, 1:23-1:200, 1:24-1:200, 1:25-1:200, 1:26-1:200, 1:27-1:200, 1:28-1:200, 1:29-1:200, 1:30-1:200, 1:35-1:200, 1:40-1:200, 1:45-1:200, 1:50-1:200, 1:55-1:200, 1:60-1:200, 1:65-1:200, 1:70-1:200, 1:75-1:200, 1:80-1:200, 1:85-1:200, 1:90-1:200, 1:95-1:200, 1:100-1:200, 1:110-1:200, 1:120-1:200, 1:130-1:200, 1:140-1:200, 1:150-1:200, 1:160-1:200, 1:170-1:200, 1:180-1:200, 1:190-1:200, or 1:200).

The alcohol solvent provided herein has a definition known in the art, and preferable alcohol solvents include but not limited to methanol, ethanol, n-propanol, isopropanol, n-butanol, and sec-butanol.

The ester solvent provided herein has a definition known in the art, and preferable ester solvents include but not limited to ethyl formate, propyl formate, isopropyl formate, methyl acetate, ethyl acetate, and isopropyl acetate.

The nitrile solvent provided herein has a definition known in the art, and preferable nitrile solvents include but not limited to acetonitrile, propionitrile, butyronitrile, and isobutyronitrile.

The ketone solvent provided herein has a definition known in the art, and preferable ketone solvents include but not limited to acetone, butanone, and 2-pentanone.

The ether solvent provided herein has a definition known in the art, and preferable ether solvents include but not limited to ethyl ether, isopropyl ether, methyl tert-butyl ether, tetrahydrofuran, or 1,4-dioxane.

The halogenated alkane solvent provided herein has a definition known in the art, and preferable halogenated alkane solvents include but not limited to dichloromethane and chloroform.

The alkane solvent provided herein has a definition known in the art, and preferable alkanes solvents include but not limited to n-hexane and n-heptane.

The halogenated fatty alcohol solvent provided herein has a definition known in the art, and preferable halogenated fatty alcohols include but not limited to trifluoroethanol.

The aromatic solvent provided herein has a definition known in the art, and preferable aromatic solvents include but not limited to toluene and ethylbenzene.

The alicyclic hydrocarbon solvent provided herein has a definition known in the art, and preferable alicyclic hydrocarbon solvents include but not limited to cyclohexane and methylcyclohexane.

The fatty acid solvent provided herein has a definition known in the art, and preferable fatty acid solvents include but not limited to acetic acid.

The water-saturated sec-butanol provided herein has a definition known in the art and can be prepared according to conventional techniques in the art.

The water-saturated ester solvent provided herein includes but not limited to water-saturated ethyl acetate and can be prepared according to conventional techniques in the art.

In the method provided herein, 3-((L-valyl)amino)-1-propanesulfonic acid in the 3-((L-valyl)amino)-1-propanesulfonic acid in the suspension solution or solution may derive from amorphous form of 3-((L-valyl)amino)-1-propanesulfonic acid.

The Crystalline Form I of the present invention herein can be prepared by applying the crystallization conditions of the present invention, via appropriate amendments, to a volatile crystallization method, a slurry crystallization method, an anti-solvent crystallization method, a cooling crystallization method, or a gas-liquid diffusion crystallization method. The operational approaches of said volatile crystallization method, said slurry crystallization method, said anti-solvent crystallization method, said cooling crystallization method, or said gas-liquid diffusion crystallization method are conventional technical means in the art.

According to the method provided herein, after crystals are precipitated, preferably, the crystals are separated from the solution. A separation method may be any conventional separation method known in the art and includes but not limited to (preferably) filtering or centrifuging. The resulting separated solid is optionally washed by using a solvent that can be selected from a group consisting of alcohol, ether, alkane, and halogenated alkane, and then dried to obtain said crystallization form of the compound provided herein. The drying includes but not limited to drying via using a drying agent or under vacuum or environmental pressure. For example, drying is performed at a temperature of about 20-60° C. under vacuum, drying is performed at room temperature, or natural volatilization to dryness is conducted at room temperature; the drying temperature is about 20-60° C., about 20-50° C., about 30-50° C., or about 20-40° C.; and the drying time has no special limitations, can be easily determined by those skilled in the art as actually desired, and for example, may be about 1 hour to 36 hours, etc.

Unless otherwise stated, the crystallization form of the compound provided herein may be subjected to a drying step. Drying can be performed at room temperature or higher temperatures. The drying temperature is about 20 to about 60° C., about 20-50° C., about 30-50° C., or about 20-40° C. The drying time has no special limitations, can be easily determined by those skilled in the art as actually desired, and for example, may be about 1 hour to 36 hours, etc.

When the reference is made with respect to the case where the crystalline form substantially exhibits an X-ray powder diffraction pattern as shown in FIG. 2, the term "substantially" means that the pattern shown in the figure must contain at least the main peaks, which, as compared to the most intense peak in the pattern, have a relative intensity of greater than 10%, especially greater than 20%. However, those skilled in the art will realize that the relative intensities in the X-ray powder diffraction pattern may be subject to strong intensity variations due to preferred orientation effects.

"The starting melt temperature" refers to a point where a significant change occurs from a baseline in the DSC curves.

"The peak temperature" refers to a peak of an endothermic peak or an exothermic peak in the DSC curves.

The "Crystalline Form I" herein can be used interchangeably with a "crystalline form" and refers to a crystalline form of the compound 3-((L-valyl)amino)-1-propanesulfonic acid as proved by characterization of the shown X-ray powder diffraction pattern.

Yet another object of the present invention is to provide a pharmaceutical composition comprising the crystalline form of compound 3-((L-valyl)amino)-1-propanesulfonic acid as described above, and a pharmaceutically acceptable carrier.

The Crystalline Form I prepared by the method provided herein is suitably prepared into various dosage forms, including but not limited to conventional solid oral dosage forms, such as granules, tablets, capsule, and pills; conventional liquid oral dosage forms, such as suspensions, emulsions, and syrups; and conventional injection dosage forms, such as freeze-dried compositions. As desired, those skilled in the art can formulate the Crystalline Form I of the compound into conventional, dispersible, chewable, orally disintegrating or quickly dissolving dosage forms. The administration routes include but not limited to common administration routes in the art, such as oral, parenteral, intravenous, intraperitoneal, intramuscular, sublingual, topical or nasal administration, and inhalation administration.

The present invention further provides use of the crystalline form of compound 3-((L-valyl)amino)-1-propanesulfonic acid as described above or the pharmaceutical composition as described above in preparation of a medication for prevention or treatment of an amyloid-β related disease in a subject in need thereof.

In an embodiment, preferably, said amyloid-β related disease is Alzheimer's disease, mild cognitive impairment (MCI), Down's syndrome, Hereditary Cerebral Hemorrhage with Amyloidosis of the Dutch-Type, cerebral amyloid angiopathy, a degenerative dementia, a dementia of mixed vascular and degenerative origin, dementia associated with Parkinson's disease, dementia associated with progressive supranuclear palsy, dementia associated with cortical basal degeneration, or dementia associated with diffuse Lewy body type of Alzheimer's disease.

In an embodiment, preferably, said amyloid-β related disease is Alzheimer's disease, mild cognitive impairment, cerebral amyloid angiopathy, or degenerative dementia.

In an embodiment, preferably, said amyloid-β related disease is Alzheimer's disease.

In an embodiment, preferably, said subject is an ApoE4 positive (also referred to herein as "ApoE4+" or simply "ApoE4") subject. Said subject has at least one ε4 allele of the apolipoprotein E (ApoE) gene. An ApoE4 positive subject may carry one or two copies of the ApoE4 allele. The ε4 allele of apolipoprotein E gene is the strongest genetic risk factor for patients with late-onset Alzheimer's disease (AD). AD patients with at least one ε4 allele account for 50%-60% of AD cases vs. 25% prevalence in healthy individuals. ApoE4+ AD patients suffer from risks of decreased age of onset, increased severity and accelerated progression of AD. Subjects with two ε4 alleles account for 10%-14% of the total number of AD patients and exhibit an even more aggressive disease progression. ε4 allele leads to an increased brain Aβ amyloid deposition, increased CSF tau and p-tau, and faster cognitive decline. In addition, demented patients carrying one or two ε4 alleles of ApoE are more likely to have AD, resulting in a significantly reduced rate of disease misdiagnosis in clinical studies (2% in ApoE4 patients vs. 42% in non-ApoE4 patients).

As used herein, the term "subject" includes living organisms with an amyloid-β related disease, or who are susceptible to or at risk of an amyloid-β related disease, e.g., due to a genetic predisposition or mutation. Examples of subjects include humans, monkeys, cows, rabbits, sheep, goats, pigs, dogs, cats, rats, mice, and transgenic species thereof. The term "subject" generally includes animals susceptible to states characterized by an amyloid-β related disease, e.g., mammals, e.g., primates and humans. The animal can also be an animal model for a disorder, e.g., a transgenic mouse model, and the like.

In an embodiment, said crystalline form of compound 3-((L-valyl)amino)-1-propanesulfonic acid and the pharmaceutical composition comprising the crystalline form may be administered using any suitable route or means, such as without limitation via oral, parenteral, intravenous, intraperitoneal, intramuscular, sublingual, topical, or nasal administration, via inhalation, or via such other routes as are known in the art.

It should be understood that the dosage or amount of compound and/or composition used, alone or in combination with one or more active compounds to be administered, depends on the individual case and is, as is customary, to be adapted to the individual circumstances to achieve an optimum effect. Dosing and administration regimens are within the purview of those skilled in the art, and appropriate doses depend upon a number of factors within the knowledge of the ordinarily skilled physician, veterinarian, or researcher (e.g., see Wells et al. eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000)).

It should be understood that compounds and/or compositions provided herein may be used alone or in combination with other therapies. Non-limiting examples of other amyloid-β related disease therapies include cognitive enhancers (e.g., acetylcholinesterase inhibitors, NMDA receptor antagonists), other amyloid-β binding compounds, and so on. Thus, compounds and/or compositions described herein may be administered alone or in combination with one or more additional therapy that may be available over-the-counter or by prescription. The latter can be administered before, after or simultaneously with the administration of the compounds and/or compositions described herein. U.S. Patent Application Publication No. 2005/0031651 (incorporated herein by reference) provides a long but non-exhaustive list of "therapeutic drugs" that can be useful, in combination, according to the invention. Non-limiting examples of therapeutic drugs to be used with the compounds or pharmaceutical compositions provided herein are therapeutic drugs useful in the prevention or treatment of Alzheimer's Disease (AD) or its symptoms, including but not limited to donepezil (Aricept™), memantine (Namenda™), rivastigmine (Exelon™), Galanthamine (Reminyl™) and R-flurbiprofen (Flurizan™). The compounds and compositions according to the present invention could also be combined with vaccines and antibodies for the prevention or treatment of AD.

The crystalline form of 3-((L-valyl)amino)-1-propanesulfonic acid provided herein has such advantages as high purity, good stability, low hygroscopicity, good solubility, good optical properties, better particle morphology, better flow properties, and improved dissolution properties and bioavailability.

The preparation method of the crystalline form is simple, the solvent is cheap and easy to obtain, and the crystallization conditions are mild. Under the solvent system and operation processes of the method provided herein, technological operation can be simplified, and a single Crystalline Form I of 3-((L-valyl)amino)-1-propanesulfonic acid can be obtained in high yield.

The use of the word "a" or "an" when used in conjunction with the term "comprising" or a noun word in the claims and/or the specification may mean "one", but it is also consistent with the meaning of "one or more", "at least one", and "one or more than one". Similarly, the word "another" or "other" may mean at least a second or more.

Unless used regarding temperatures, the term "about" placed before a numerical value "X" refers in the present application to an interval extending from X minus 10% of X to X plus 10% of X, and preferably to an interval extending from X minus 5% of X to X plus 5% of X. In the particular case of temperatures, the term "about" placed before a temperature "Y" refers in the present application to an interval extending from the temperature Y minus 3° C. to Y plus 3° C., and preferably to an interval extending from Y minus 2° C. to Y plus 2° C.

DETAILED DESCRIPTION

The present invention is further illustrated in detail by the following examples. Temperature is expressed in degrees Celsius. Unless stated otherwise, room temperature is in the range of 10-30° C. and the percentage is expressed by weight. In the following examples, the experimental methods without specific conditions are carried out according to conventional procedures and conditions, or according to the product instructions.

Abbreviations:
DSC differential scanning calorimetry
RH relative humidity
XRD or XRPD X-ray powder diffraction
DCC N,N'-dicyclohexylcarbodiimide
eq equivalent The X-ray powder diffraction (XRPD) test instrument involved herein is Bruker D8 Advance diffractometer; detection conditions: Cu Kα radiation with X-ray of 1.54Å, 40 kV/40 mA; detection angle: 3-40°2θ, scanning step: 0.02°2θ; and scanning speed: 0.2 s.step⁻¹. Detection of environmental conditions: temperature=21° C., humidity=50%.

The X-ray single crystal diffraction analysis instrument involved herein is BrukerVenture; detection conditions: detection is carried out at a wavelength of 0.71073 Å at a temperature of 180 K.

The differential scanning calorimetry (DSC) instrument is the Q200 DSC instrument from TA Instruments; detection conditions: an aluminum crucible (with cover, but without perforation), a protective atmosphere of nitrogen, a gas flow rate of 40 mL/min, and the following common detection method: equilibrate at 20° C., and ramp rate of 10° C./min to 340° C. Detection of environmental conditions: temperature=20° C., humidity=56%.

The thermogravimetric analyzer (TGA) involved herein is Q500TGA from TA Instruments; detection conditions: a platinum crucible, a protective atmosphere of nitrogen, a gas flow rate of 40 mL/min; and the following detection method: a Hi-Res sensitivity of 3.0, ramp 10.00° C./min, res 5.0 to 120.00° C., and ramp 10.00° C./min to 350° C.

The polarization microscope (PLM) graph involved herein is derived from an XP-500E heating stage polarization microscope (from Shanghai Changfang Optical instrument Co., Ltd.). A small amount of powder samples were taken and placed on a glass slide, a little mineral oil was added dropwise to the glass slide to better disperse the powder samples, and a cover glass was taken to cover the glass slide. Then, a sample was placed on an object stage of the XP-500E heating stage polarization microscope, and an appearance of the sample was observed at an appropriate amplification factor selected and photographed.

The Fourier Transform infrared (FT-IR) spectrometer involved herein is Bruker Tensor 27 (control software/analysis software: OPUS); detecton method: an ATR method; collected wavelength range: 600-4000 cm⁻¹; scanning time: 32 s; and a resolution ratio: 4 cm⁻¹.

EXAMPLE 1

Preparation of 3-((L-valyl)amino)-1-propanesulfonic Acid 1 g of 3((L-valypamino)-1-propanesulfonic acid was dissolved in 5 mL water and subjected to concentration under reduced pressure to obtain 1 g of an amorphous solid compound.

Figure 1:
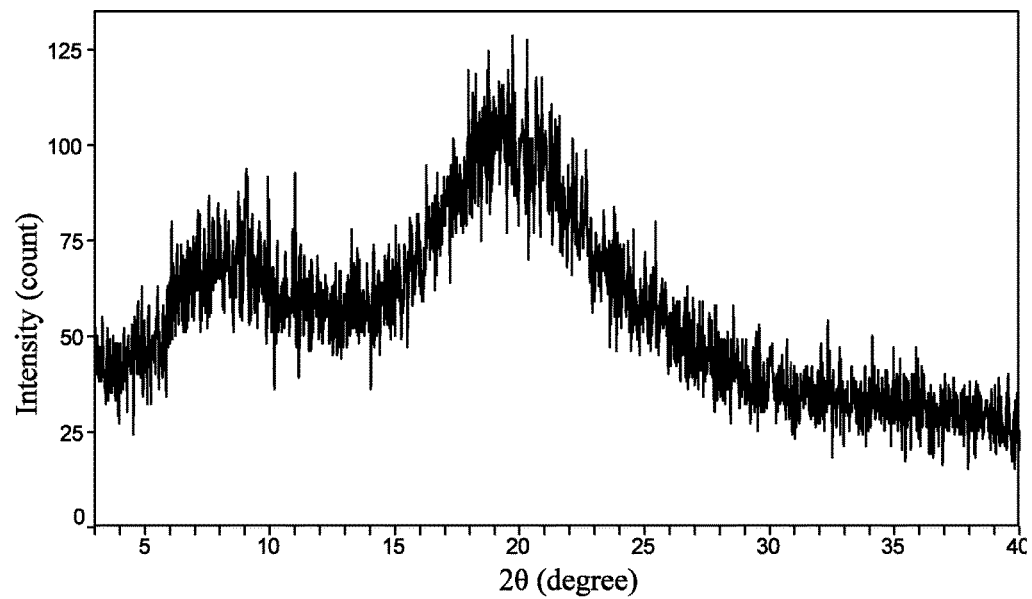
FIG. 1 is an X-ray powder diffraction (XRD) pattern of an amorphous compound 3-((L-valyl)amino)-1-propanesulfonic acid in Example 1.

The X-ray powder diffraction (XRD) pattern of the amorphous solid is as shown in FIG. 1.

EXAMPLE 2

Preparation of the Crystalline Form I of 3-((L-valyl)amino)-1-propanesulfonic Acid A solvent system of water/ethanol/acetone (1.0 mL/2.0 mL/2.0 mL) having a total volume of 5.0 mL was added to 100 mg of the amorphous solid compound of 3-((L-valyl)amino)-1-propanesulfonic acid obtained according to Example 1, wherein solvents were added in the sequence of water (i.e., a first solvent), ethanol (i.e., a second solvent), and acetone (i.e., a third solvent) to obtain a clear solution, and after filtration the filtrate was placed at room temperature (crystallization temperature) and naturally evaporated to dryness to obtain 95 mg of granular crystals, i.e., the Crystalline Form I, having a yield of 95% and a purity of greater than 99%.

EXAMPLE 3

Determination of Characterization of Crystalline Form I of 3-((L-valyl)amino)-1-propanesulfonic Acid Obtained According to Example 2

1. X-Ray Powder Diffraction of the Crystalline Form I

The determination was carried out using the aforementioned instruments, determination methods, operating conditions, and parameters. The result is shown in FIG. 2, and those specific data are shown in Table 1:

TABLE 1

Figure 2:
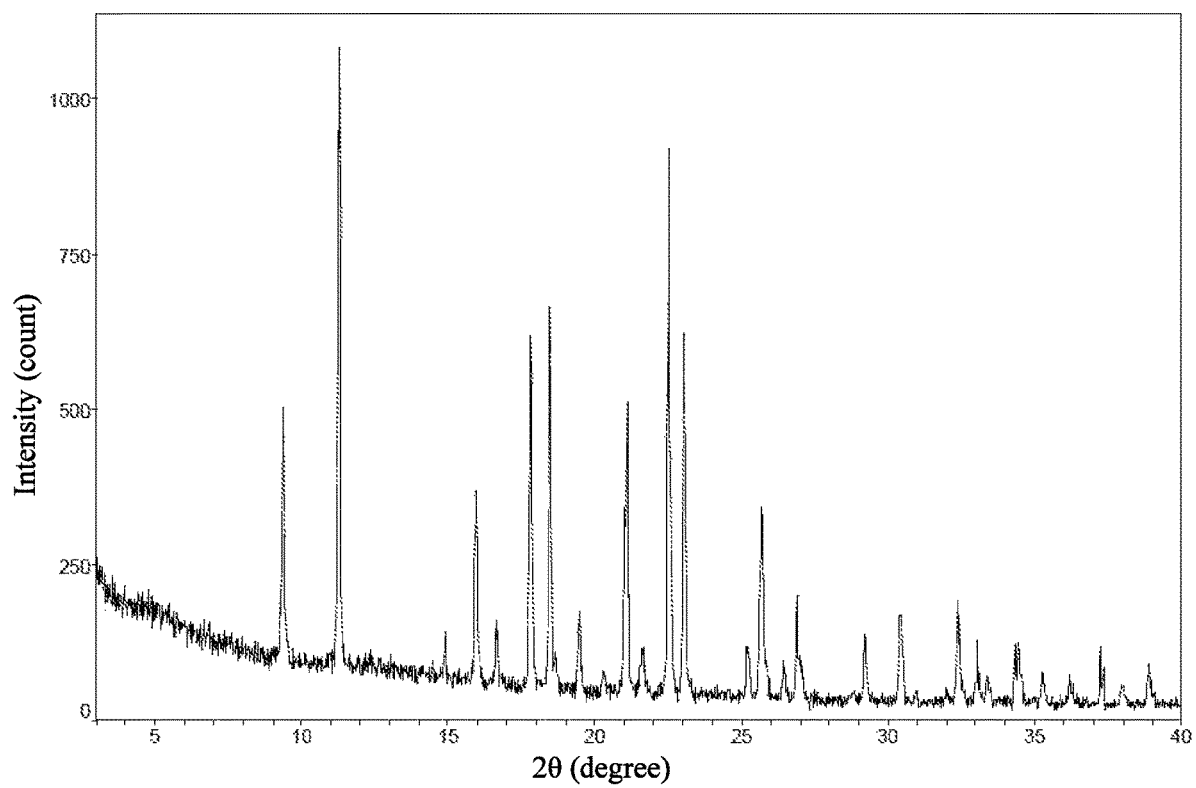
FIG. 2 is an X-ray powder diffraction (XRD) pattern of the Crystalline Form I of 3-((L-valyl)amino)-1-propanesulfonic acid prepared in Example 2 of the present invention.

Data related to X-ray powder diffraction in FIG. 2

| Peak No. | 2θ diffraction angle (°) | Interplanar Spacing (Å) | Peak Height | Peak Height Relative Intensity (I %) | Peak Area | Peak Area Relative Intensity (I %) |
| --- | --- | --- | --- | --- | --- | --- |
| 1 | 9.38 | 9.421 | 409 | 41.3 | 2512 | 45.6 |
| 2 | 11.294 | 7.8278 | 991 | 100 | 5505 | 100 |
| 3 | 14.894 | 5.9432 | 78 | 7.9 | 483 | 8.8 |
| 4 | 15.939 | 5.5557 | 312 | 31.5 | 2032 | 36.9 |
| 5 | 16.658 | 5.3175 | 107 | 10.8 | 799 | 14.5 |
| 6 | 17.804 | 4.9778 | 570 | 57.5 | 3125 | 56.8 |
| 7 | 18.465 | 4.8011 | 614 | 62 | 3258 | 59.2 |
| 8 | 19.473 | 4.5547 | 122 | 12.3 | 630 | 11.4 |
| 9 | 20.285 | 4.3743 | 30 | 3 | 88 | 1.6 |
| 10 | 21.098 | 4.2075 | 467 | 47.1 | 2616 | 47.5 |
| 11 | 21.659 | 4.0997 | 79 | 8 | 919 | 16.7 |
| 12 | 22.539 | 3.9416 | 884 | 89.2 | 4966 | 90.2 |
| 13 | 23.033 | 3.8582 | 580 | 58.5 | 3276 | 59.5 |
| 14 | 25.192 | 3.5321 | 81 | 8.2 | 542 | 9.8 |
| 15 | 25.668 | 3.4677 | 306 | 30.9 | 2570 | 46.7 |
| 16 | 26.429 | 3.3695 | 61 | 6.2 | 416 | 7.6 |
| 17 | 26.901 | 3.3116 | 166 | 16.8 | 1116 | 20.3 |
| 18 | 29.204 | 3.0554 | 112 | 11.3 | 1051 | 19.1 |
| 19 | 30.427 | 2.9354 | 143 | 14.4 | 1264 | 23 |
| 20 | 32.367 | 2.7637 | 164 | 16.5 | 1369 | 24.9 |
| 21 | 33.04 | 2.7089 | 100 | 10.1 | 543 | 9.9 |
| 22 | 33.381 | 2.682 | 40 | 4 | 436 | 7.9 |
| 23 | 34.445 | 2.6015 | 95 | 9.6 | 856 | 15.5 |

TABLE 1-continued

Data related to X-ray powder diffraction in FIG. 2

| Peak No. | 2θ diffraction angle (°) | Interplanar Spacing (Å) | Peak Height | Peak Height Relative Intensity (I %) | Peak Area | Peak Area Relative Intensity (I %) |
|---|---|---|---|---|---|---|
| 24 | 35.265 | 2.5429 | 51 | 5.1 | 314 | 5.7 |
| 25 | 36.205 | 2.479 | 47 | 4.7 | 339 | 6.2 |
| 26 | 37.241 | 2.4124 | 86 | 8.7 | 248 | 4.5 |
| 27 | 38.885 | 2.3141 | 67 | 6.8 | 506 | 9.2 |

2. X-Ray Single Crystal Diffraction Analysis of Said Crystalline Form I

Figure 3:
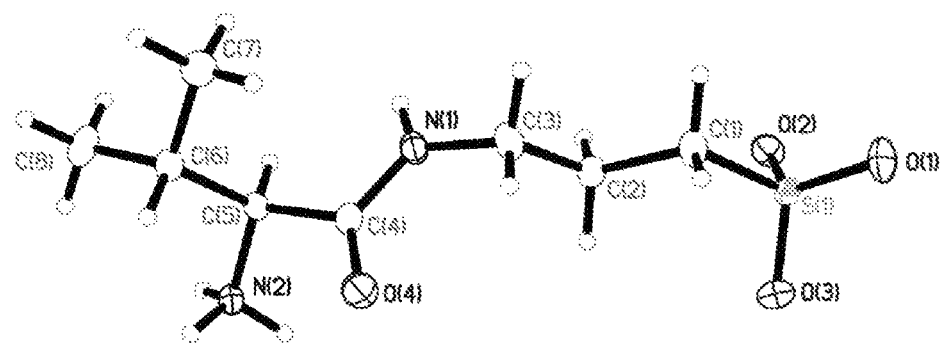
FIG. 3 is a diagram showing the structure and atomic number of the Crystalline Form I of 3-((L-valyl)amino)-1-propanesulfonic acid according to the present invention.
Figure 4:
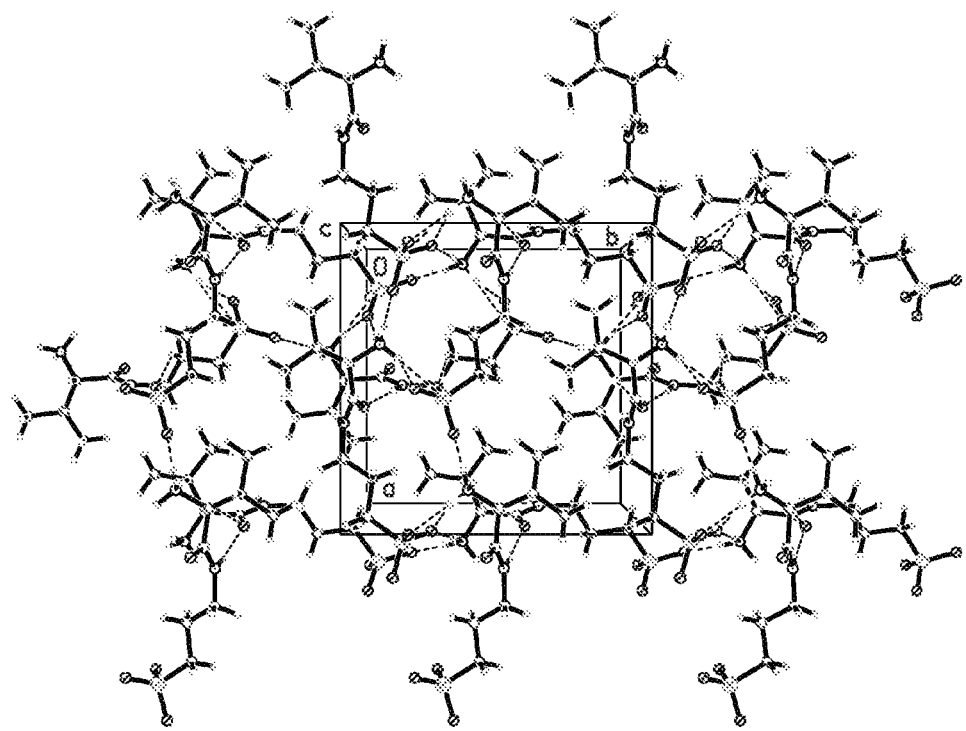
FIG. 4 is a unit cell packing diagram of the Crystalline Form I of 3-((L-valyl)amino)-1-propanesulfonic acid according to the present invention.

The determination was carried out using the aforementioned instruments, determination methods, operating conditions, and parameters. The results are shown below and in Tables 2-3 and FIGS. 3-4.

The compound 3-((L-valyl)amino)-1-propanesulfonic acid according to the present invention has the molecular formula of $C_8H_{18}N_2O_4S$, a molecular weight of 238.30, a density of 1.384 Mg/m$^3$, F(000)=1024. The Crystalline Form I is a white crystal and has a crystal size of 0.300× 0.300×0.100 mm$^3$. The Crystalline Form I belongs to a tetragonal system and has a space group of P4$_3$2$_1$2. The unit cell dimensions measured at a wavelength of 0.71073 Å at a temperature of 180 K are as follows:

a=11.1988(4) Å, α=90°, b=11.1988(4) Å, β=90°, c=18.2429(7) Å, γ=90°, Z=8, unit cell volume of 2287.90(19) Å$^3$.

TABLE 2

Atomic coordinates (×10$^4$) and equivalent isotropic displacement parameters (Å$^2$ × 10$^3$) of Crystalline Form I of 3-((L-valyl)amino)-1-propanesulfonic acid

| | x | y | z | U(eq) |
|---|---|---|---|---|
| S(1) | 4282(1) | 6791(1) | 1087(1) | 16(1) |
| O(1) | 3036(1) | 6442(1) | 1154(1) | 27(1) |
| O(2) | 4639(1) | 7029(1) | 335(1) | 23(1) |
| O(3) | 4616(1) | 7782(1) | 1564(1) | 28(1) |
| O(4) | 8934(1) | 5299(1) | 2681(1) | 23(1) |
| N(1) | 8400(1) | 4697(2) | 1541(1) | 19(1) |
| N(2) | 11162(1) | 5927(1) | 2107(1) | 16(1) |
| C(1) | 5126(2) | 5544(2) | 1385(1) | 22(1) |
| C(2) | 6471(2) | 5727(2) | 1331(1) | 19(1) |
| C(3) | 7121(2) | 4670(2) | 1676(1) | 23(1) |
| C(4) | 9192(2) | 4988(2) | 2054(1) | 16(1) |
| C(5) | 10494(2) | 4864(2) | 1822(1) | 15(1) |
| C(6) | 11039(2) | 3698(2) | 2121(1) | 19(1) |
| C(7) | 10259(2) | 2622(2) | 1935(1) | 26(1) |
| C(8) | 12309(2) | 3520(2) | 1835(1) | 31(1) |

TABLE 3

Hydrogen coordinates (×10$^4$) and equivalent isotropic displacement parameters (Å$^2$ × 10$^3$) of Crystalline Form I of 3-((L-valyl)amino)-1-propanesulfonic acid

| | x | y | z | U(eq) |
|---|---|---|---|---|
| H(1A) | 8662 | 4512 | 1101 | 23 |
| H(2A) | 11787 | 6091 | 1805 | 25 |
| H(2B) | 11439 | 5767 | 2566 | 25 |
| H(2C) | 10663 | 6569 | 2125 | 25 |
| H(1B) | 4917 | 5368 | 1902 | 26 |
| H(1C) | 4901 | 4840 | 1087 | 26 |
| H(2D) | 6698 | 6472 | 1587 | 23 |
| H(2E) | 6706 | 5803 | 810 | 23 |
| H(3A) | 6978 | 4673 | 2212 | 28 |

TABLE 3-continued

Hydrogen coordinates (×10$^4$) and equivalent isotropic displacement parameters (Å$^2$ × 10$^3$) of Crystalline Form I of 3-((L-valyl)amino)-1-propanesulfonic acid

| | x | y | z | U(eq) |
|---|---|---|---|---|
| H(3B) | 6787 | 3919 | 1476 | 28 |
| H(5A) | 10540 | 4857 | 1274 | 18 |
| H(6A) | 11080 | 3766 | 2667 | 23 |
| H(7B) | 9482 | 2706 | 2177 | 39 |
| H(7C) | 10650 | 1891 | 2107 | 39 |
| H(7A) | 10144 | 2579 | 1403 | 39 |
| H(8C) | 12807 | 4196 | 1987 | 46 |
| H(8A) | 12295 | 3472 | 1299 | 46 |
| H(8B) | 12639 | 2779 | 2037 | 46 |

3. Differential Scanning Calorimetry (DSC) of the Crystalline Form I

Figure 5:
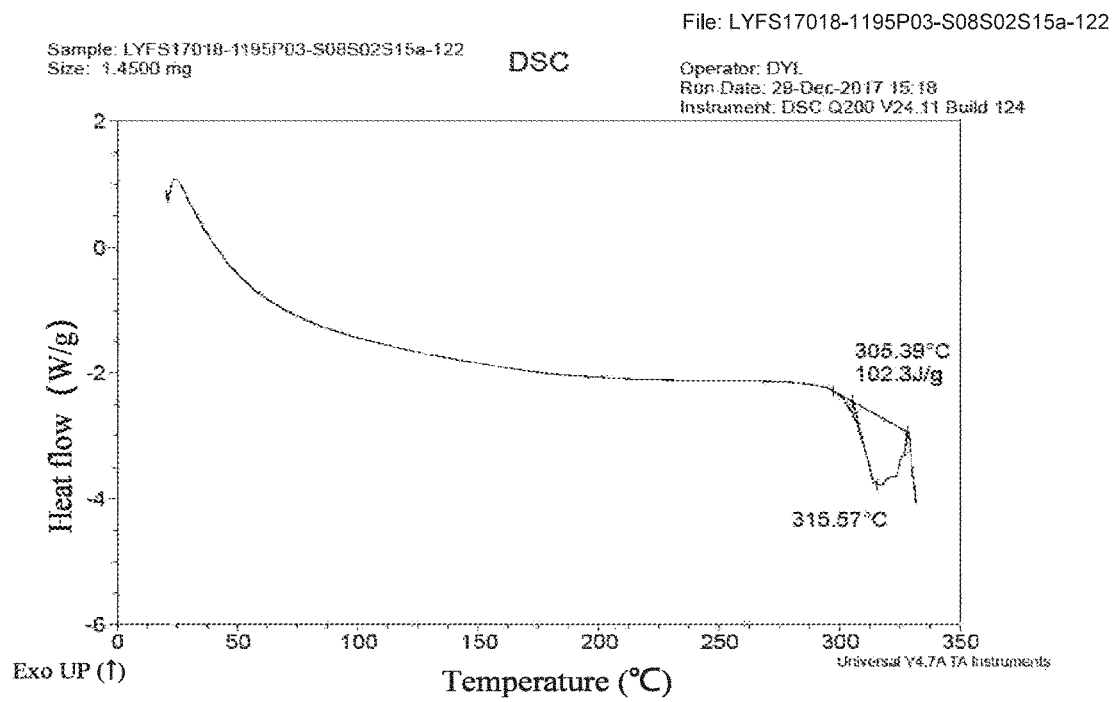
FIG. 5 illustrates differential scanning calorimetry (DSC) curves of the Crystalline Form I of 3-((L-valyl)amino)-1-propanesulfonic acid prepared in Example 2 of the present invention. In the DSC curves, the Crystalline Form I has a starting melt temperature of about 305° C. and a peak temperature of about 316° C. .

The determination was carried out using the aforementioned instruments, determination methods, operating conditions, and parameters. The results are shown in FIG. 5. In the DSC curves, its starting melt temperature is about 305° C., and the peak temperature is about 316° C.

4. Thermogravimetric Analysis (TGA) of the Crystalline Form I

Figure 6:
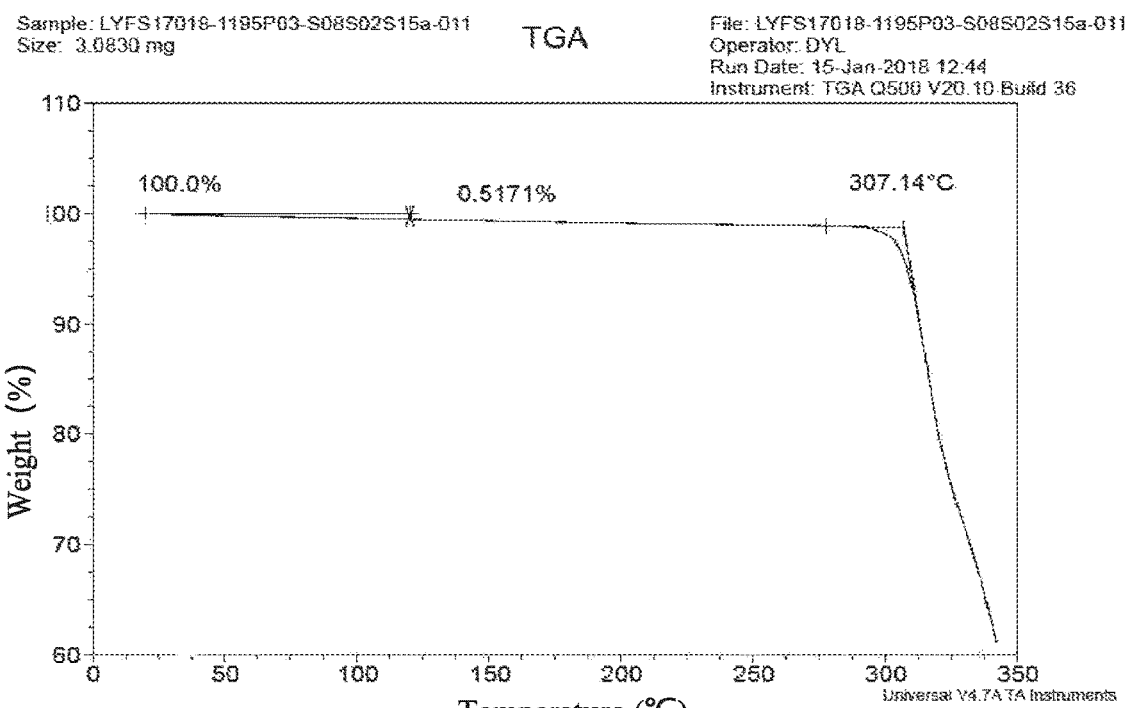
FIG. 6 is a thermogravimetric analysis diagram of the Crystalline Form I of 3-((L-valyl)amino)-1-propanesulfonic acid prepared in Example 2 of the present invention, which shows that the crystalline form has a slow weight loss of about 0.5wt % before about 120° C., showing that it is an anhydrate; and the decomposition temperature is about 307° C.

The determination was carried out using the aforementioned instruments, determination methods, operating conditions, and parameters. The results are shown in FIG. 6. The TGA diagram shows that the crystalline form has a slow weight loss of about 0.5wt % before about 120° C., showing that it is an anhydrate; and the decomposition temperature is about 307° C.

5. Polarization Microscope (PLM) Detection Method of the Crystalline Form I

Figure 7:
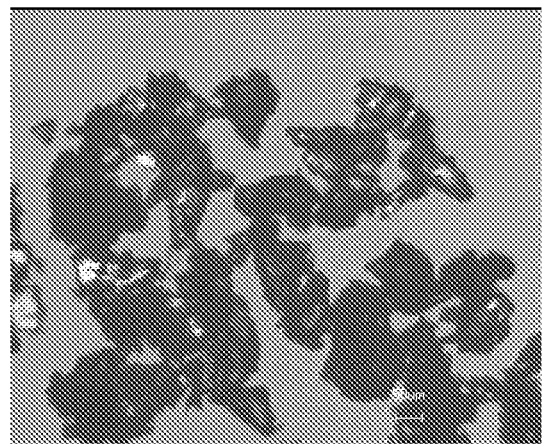
FIG. 7 is a PLM representation diagram of the Crystalline Form I of 3-((L-valyl)amino)-1-propanesulfonic acid prepared in Example 2 of the present invention, which shows that the Crystalline Form I of the compound prepared in Example 2 is a granular crystalline form having good uniformity.

The determination was carried out using the aforementioned instruments, determination methods, operating conditions, and parameters (ocular lens times=10 times, objective lens times=4 times etc.). The results are shown in FIG. 7. The PLM graph shows that the compound crystals prepared in Example 2 are granular crystals having good uniformity.

6. FT-IR Representation Diagram of the Crystalline Form I

Figure 8:
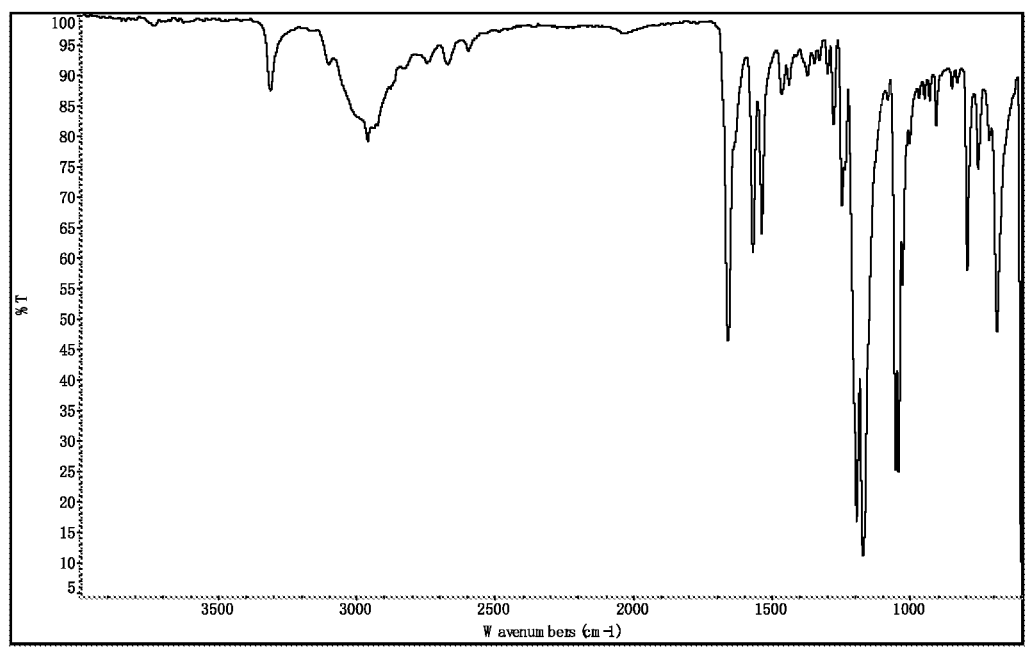
FIG. 8 is a FT-IR representation diagram of the Crystalline Form I of 3-((L-valyl)amino)-1-propanesulfonic acid prepared in Example 2 of the present invention.

The determination was carried out using the aforementioned instruments, determination methods, operating conditions, and parameters. The results are shown in FIG. 8.

EXAMPLE 4

Preparation of a Crystalline Form of 3-((L-valyl)amino)-1-propanesulfonic Acid

About 100 mg of the solid of 3((L-valyl)amino)-1-propanesulfonic acid obtained according to Example 1 was taken, and used to prepare the crystalline form of 3-((L-valyl)amino)-1-propanesulfonic acid according to the method of Example 2, except that the solvent system (a first solvent/a second solvent/a third solvent) of water/ethanol/acetone (1 mL/2 mL/1 mL) having a total volume of 4 mL was used.

95 mg of white crystals were obtained with a yield of 95% and a purity of greater than 99%, and was Crystalline Form I as characterized by XRD (not shown).

EXAMPLE 5

Preparation of a Crystalline Form of 3-((L-valyl)amino)-1-propanesulfonic Acid

About 100 mg of the solid of 3-((L-valyl)amino)-1-propanesulfonic acid in Example 1 was taken, and used to prepare the crystalline form of 3-((L-valyl)amino)-1-propanesulfonic acid according to the method of Example 2, except that the solvent system (a first solvent/a second solvent/a third solvent) of water/ethanol/acetone (1 mL/1 mL/2 mL) having a total volume of 4 mL was used.

95 mg of white crystals were obtained with a yield of 95% and a purity of greater than 99%, and was Crystalline Form I as characterized by XRD (not shown).

EXAMPLES 6-9

Preparation of crystalline forms of 3-((L-valyl)amino)-1-propanesulfonic acid under different conditions by reference to the method of Example 2 was investigated, and results were shown in Table 4 below.

TABLE 4

The results of preparation of crystalline forms of 3-((L-valyl)amino)-1-propanesulfonic acid of examples 6-9

| Examples | Solvent System (First Solvent/Second Solvent/optional Third Solvent) | Amount of Solvents (v/v(ml/ml) or v/v/v, (ml/ml/ml)) | Amount of Amorphous Solid of Example 1 (mg) | Crystallization Temperature (° C.) | Crystal Morphology | Crystalline Form |
|---|---|---|---|---|---|---|
| 6 | Water/Trifluoroethanol | 0.2/0.8 | 10 | Room Temperature | Slices | Crystalline Form I |
| 7 | Water/Isopropanol/Tetrahydrofuran | 0.2/0.2/0.6 | 10 | Room Temperature | Slices | Crystalline Form I |
| 8 | Water/Ethyl acetate/Acetonitrile | 0.2/0.2/0.6 | 10 | Room Temperature | Bulks | Crystalline Form I |
| 9 | Water/N-propanol/1,4-dioxane | 0.2/0.2/0.2 | 10 | 50° C. | Fine Powder | Crystalline Form I |

The crystal sample prepared in Examples 6-9 and the crystal sample in Example 2 have the same or similar XRD pattern (not shown), indicating that the sample of Examples 6-9 and the sample of Example 2 belong to the same crystalline form.

Figure 9:
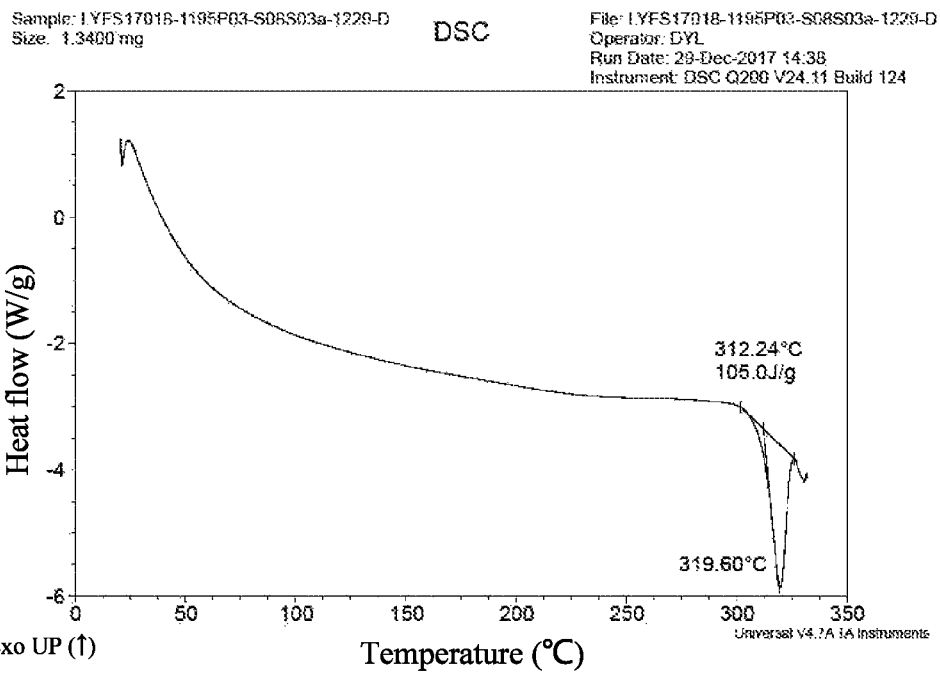
FIG. 9 illustrates differential scanning calorimetry (DSC) curves of the Crystalline Form I of 3-((L-valyl)amino)-1-propanesulfonic acid prepared in Example 6 of the present invention. In the DSC curves, the Crystalline Form I has a starting melt temperature of about 312° C. and a peak temperature of about 320° C.
Figure 10:
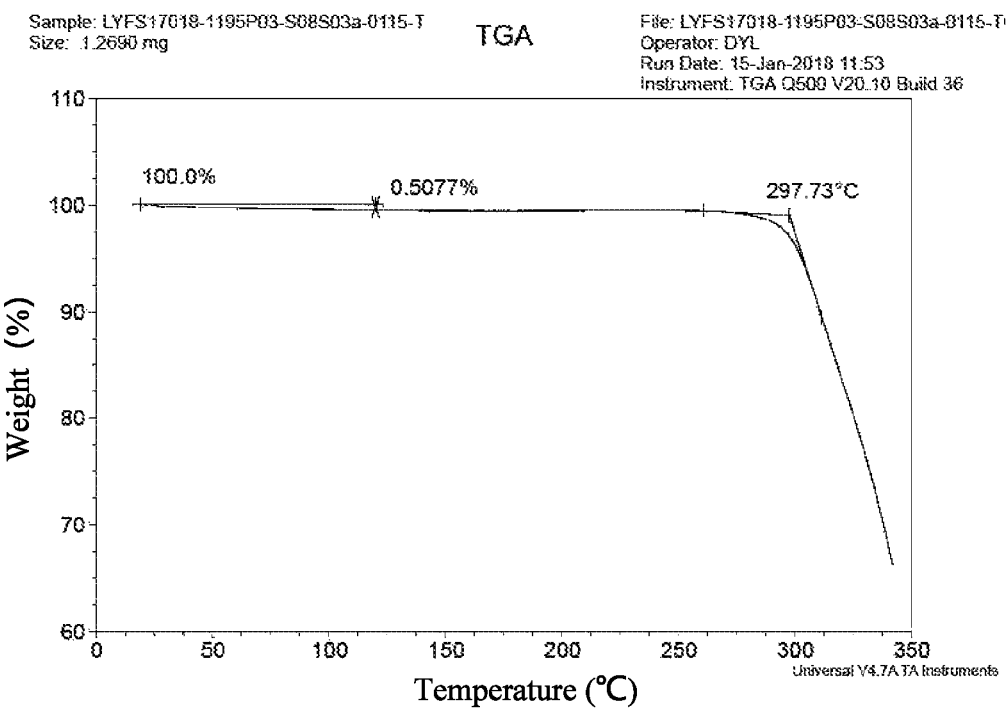
FIG. 10 is a thermogravimetric analysis diagram of the Crystalline Form I of 3-((L-valyl)amino)-1-propanesulfonic acid prepared in Example 6 of the present invention, which shows that the crystalline form has a slow weight loss of about 0.5wt % before about 120° C., showing that it is an anhydrate; and the decomposition temperature is about 300° C.

The DSC curves (see FIG. 9) of the crystal sample of Example 6 show that the starting melt temperature is about 312° C., the peak temperature is about 320° C., and its TGA diagram (see FIG. 10) indicates that the crystalline form has a slow weight loss of about 0.5wt % before about 120° C., showing that it is an anhydrate; and the decomposition temperature is about 300° C.

Figure 11:
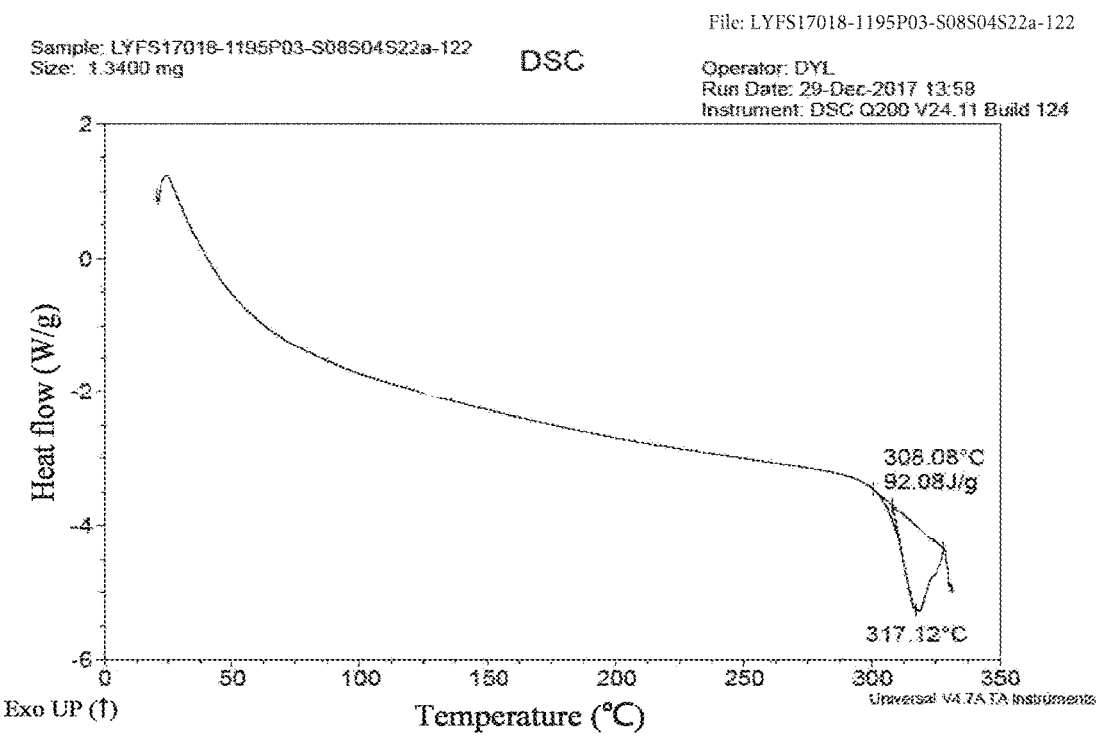
FIG. 11 illustrates differential scanning calorimetry (DSC) curves of the Crystalline Form I of 3-((L-valyl)amino)-1-propanesulfonic acid prepared in Example 7 of the present invention. In the DSC curves, the Crystalline Form I has a starting melt temperature of about 308° C. and a peak temperature of about 317° C.
Figure 12:
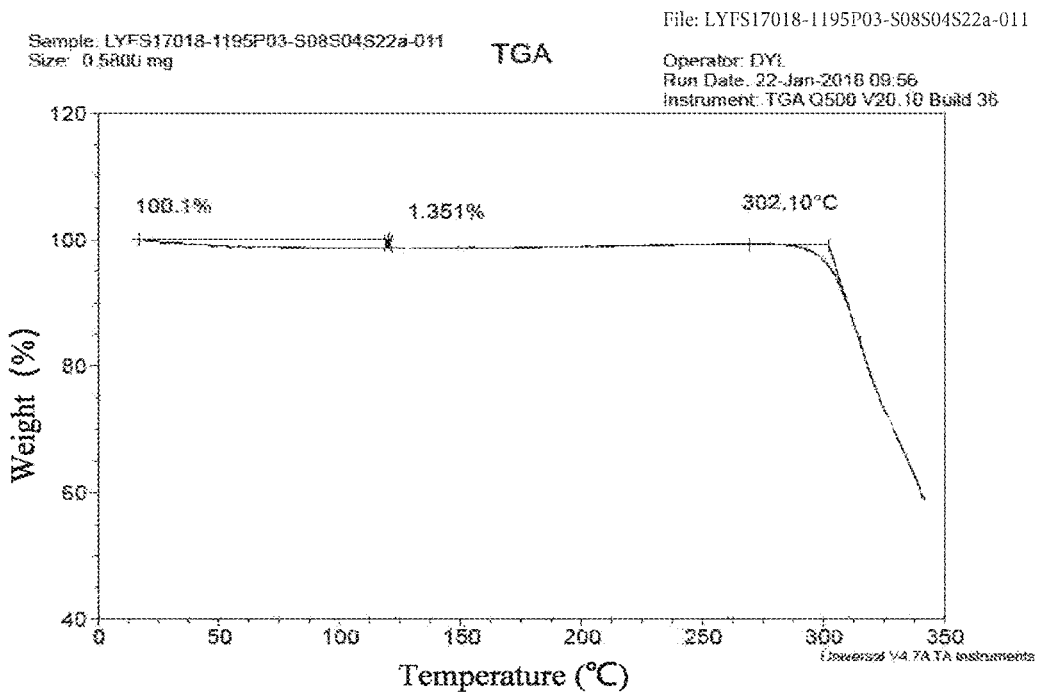
FIG. 12 is a thermogravimetric analysis diagram of the Crystalline Form I of 3-((L-valyl)amino)-1-propanesulfonic acid prepared in Example 7 of the present invention, which shows that the crystalline form has a slow weight loss of about 1.4wt % before about 120° C., showing that it is an anhydrate; and the decomposition temperature is about 302° C.

The DSC curves (see FIG. 11) of the crystal sample (No. S08S04S22a) of Example 7 show that the starting melt temperature is about 308° C., the peak temperature is about 317° C., and its TGA diagram (see FIG. 12) indicates that the crystalline form has a slow weight loss of about 1.4wt % before about 120° C., showing that it is an anhydrate; and the decomposition temperature is about 302° C.

Figure 13:
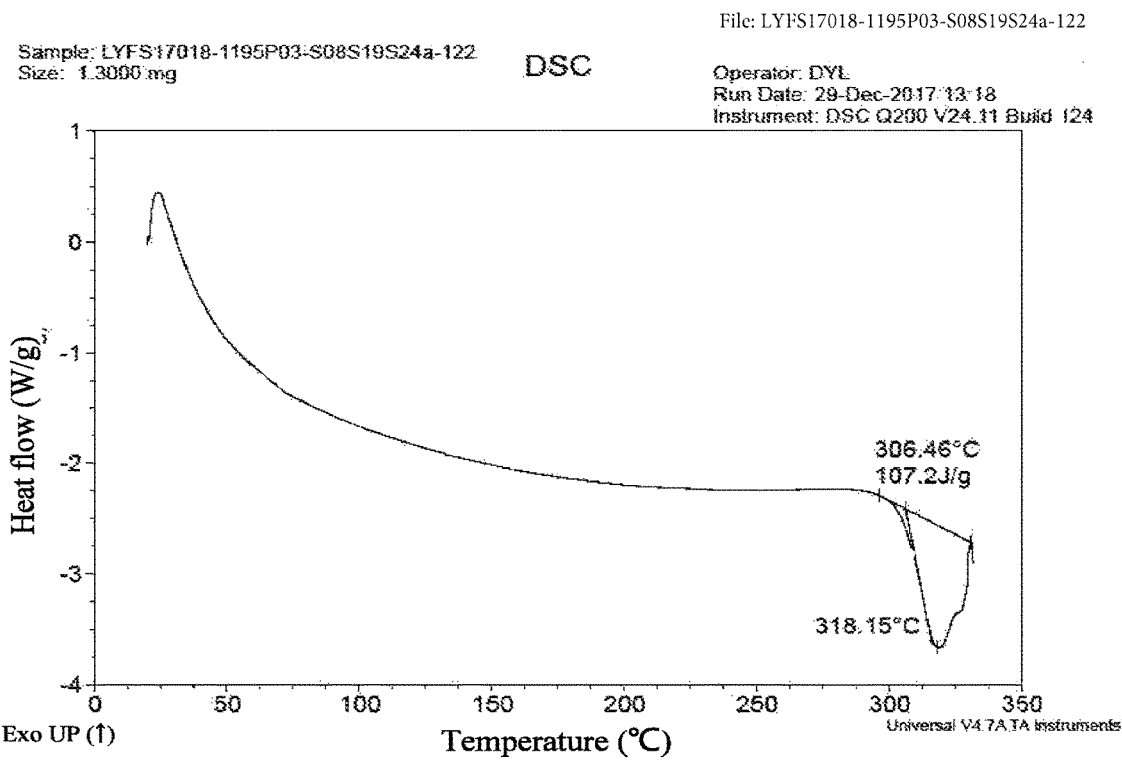
FIG. 13 illustrates differential scanning calorimetry (DSC) curves of the Crystalline Form I of 3-((L-valyl)amino)-1-propanesulfonic acid prepared in Example 8 of the present invention. In the DSC curves, the Crystalline Form I has a starting melt temperature of about 306° C. and a peak temperature of about 318° C.
Figure 14:
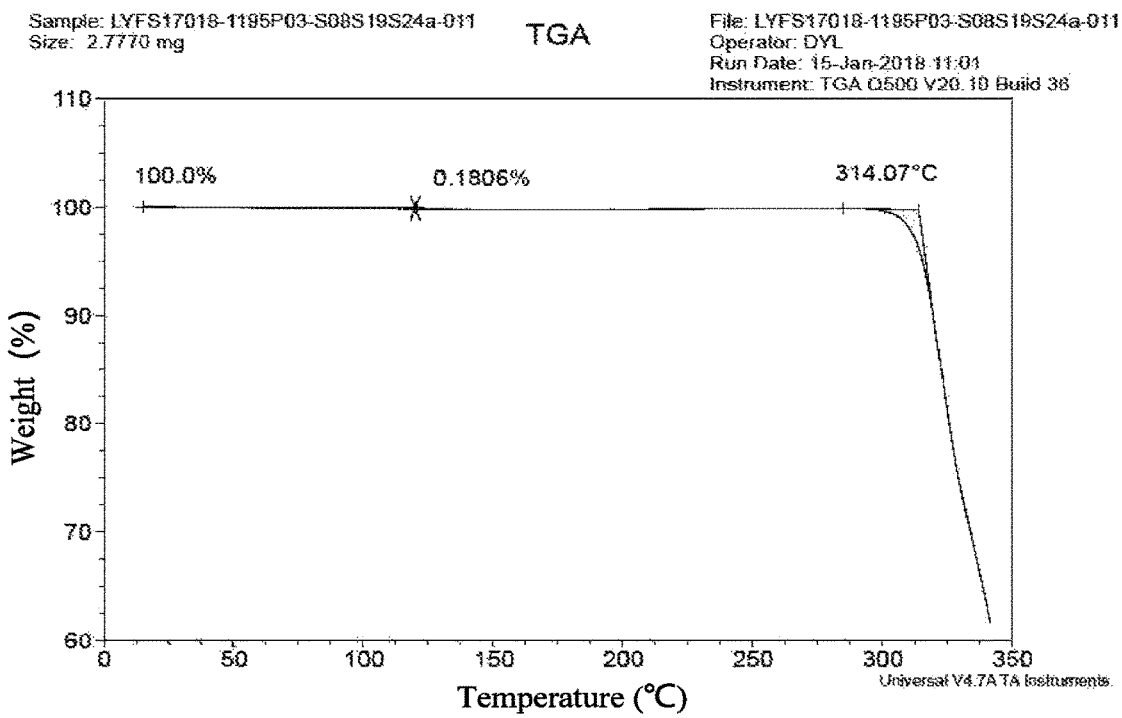
FIG. 14 is a thermogravimetric analysis diagram of the Crystalline Form I of 3-((L-valyl)amino)-1-propanesulfonic acid prepared in Example 8 of the present invention, which shows that the crystalline form has a slow weight loss of about 0.2wt % before about 120° C., showing that it is an anhydrate; and the decomposition temperature is about 314° C.

The DSC curves (see FIG. 13) of the crystal sample (No. S08S19S24a) of Example 8 show that the starting melt temperature is about 306° C., the peak temperature is about 318° C., and its TGA diagram (see FIG. 14) indicates that the crystalline form has a slow weight loss of about 0.2wt % before about 120° C., showing that it is an anhydrate; and the decomposition temperature is about 314° C.

Figure 15:
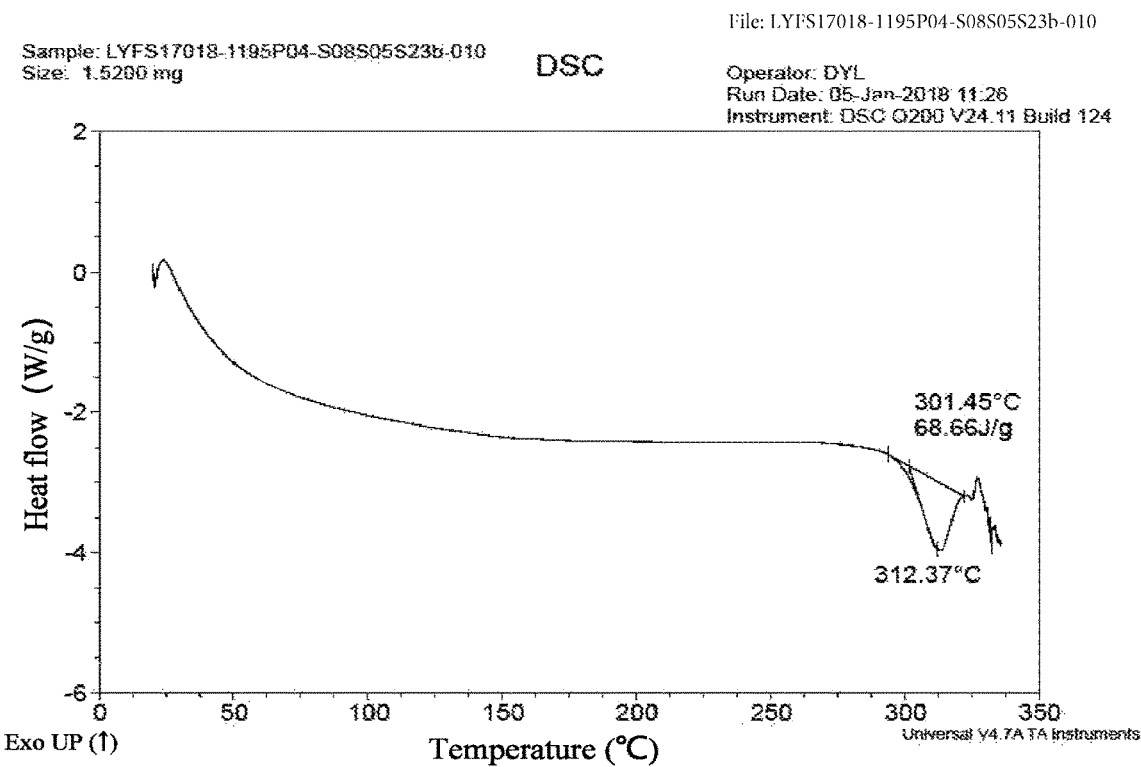
FIG. 15 illustrates differential scanning calorimetry (DSC) curves of the Crystalline Form I of 3-((L-valyl)amino)-1-propanesulfonic acid prepared in Example 9 of the present invention. In the DSC curves, the Crystalline Form I has a starting melt temperature of about 301° C. and a peak temperature of about 312° C.
Figure 16:
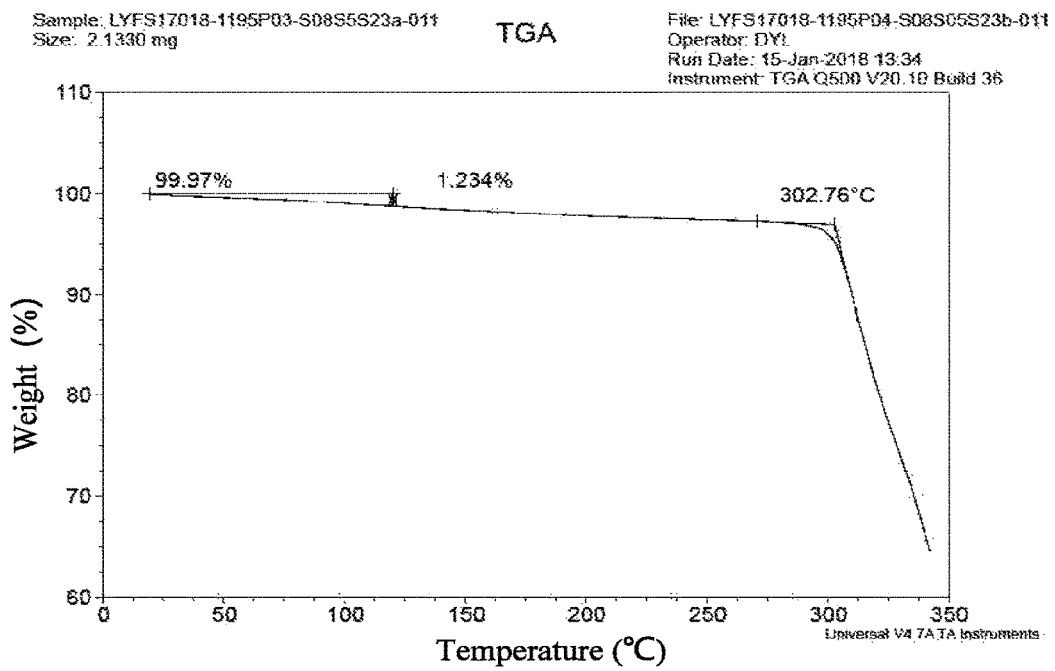
FIG. 16 is a thermogravimetric analysis diagram of the Crystalline Form I of 3-((L-valyl)amino)-1-propanesulfonic acid prepared in Example 9 of the present invention, which shows that the crystalline form has a slow weight loss of about 1.2wt % before about 120° C., showing that it is an anhydrate; and the decomposition temperature is about 303° C.

The DSC curves (see FIG. 15) of the crystal sample of Example 9 show that the starting melt temperature is about 301° C., the peak temperature is about 312° C., and its TGA diagram (see FIG. 16) indicates that the crystalline form has a slow weight loss of about 1.2wt % before about 120° C., showing that it is an anhydrate; and the decomposition temperature is about 303° C.

EXAMPLE 10

Water having a total volume of 0.2 mL was added to 10 mg of the amorphous solid of 3-((L-valyl)amino)-1-propanesulfonic acid prepared in Example 1 to obtain a clear solution, and after filtration the filtrate was placed at room temperature (crystallization temperature) and naturally evaporated to dryness to obtain 9 mg of granular crystals, i.e., the Crystalline Form I as characterized by XRD (not shown), having a yield of 90% and a purity of greater than 99%.

EXAMPLE 11

A solvent system of water/methanol (0.2 mL/0.8 mL) having a total volume of 1.0 mL was added to 10 mg of the amorphous solid of 3-((L-valyl)amino)-1-propanesulfonic acid obtained according to Example 1, wherein solvents were added in the sequence of water (i.e., a first solvent) and methanol (i.e., a second solvent) to obtain a clear solution, and the filtrate after filtration was placed at room temperature (crystallization temperature) and naturally evaporated to dryness to obtain 9 mg of granular crystals, i.e., the Crystalline Form I as characterized by XRD (not shown), having a yield of 90% and a purity of greater than 99%.

EXAMPLE 12

A solvent system (a first solvent/a second solvent/a third solvent) of water/acetone/isopropyl acetate (0.2 mL/0.6 mL/0.2 mL) having a total volume of 1.0 mL was added to 10 mg of the amorphous solid of 3-((L-valyl)amino)-1-propanesulfonic acid obtained according to Example 1, wherein solvents were added in the sequence of water (i.e., the first solvent), acetone (i.e., the second solvent), and isopropyl acetate (i.e., the third solvent) to obtain a clear solution, and the filtrate after filtration was placed at a temperature of 50° C. and evaporated to dryness to obtain 8 mg of granular crystals, i.e., the Crystalline Form I as characterized by XRD (not shown), having a yield of 80% and a purity of greater than 99%.

EXAMPLE 13

A solvent system (a first solvent/a second solvent/a third solvent) of water/acetonitrile/N,N-dimethylformamide (0.2 mL/0.4 mL/0.2 mL) having a total volume of 0.8 mL was added to 10 mg of the amorphous solid of 3-((L-valyl)amino)-1-propanesulfonic acid obtained according to Example 1, wherein solvents were added in the sequence of water (i.e., the first solvent), acetonitrile (i.e., the second solvent), and N,N-dimethylformamide (i.e., the third solvent) to obtain a clear solution, and the filtrate after filtration was placed at a temperature of 50° C. and evaporated to dryness to obtain 8 mg of granular crystals, i.e., the Crystalline Form I as characterized by XRD (not shown), having a yield of 80% and a purity of greater than 99%.

EXAMPLE 14

A solvent system of trifluoroethanol/acetonitrile/water (2.0 mL/2.0 mL/0.02 mL) having a total volume of 4.02 mL was added to 10 mg of the amorphous solid of 3-((L-valyl)amino)-1-propanesulfonic acid obtained according to Example 1, wherein solvents were added in the sequence of trifluoroethanol (i.e., the first solvent), acetonitrile (i.e., the second solvent), and water (i.e., the third solvent) to obtain a suspension solution which was stirred for 5 days at room temperature, and the resulting crystal slurry was subjected to centrifugal filtration, washing, and drying to obtain 8 mg of fine granular crystals, i.e., the Crystalline Form I as characterized by XRD (not shown), having a yield of 80% and a purity of greater than 99%.

Figure 17:
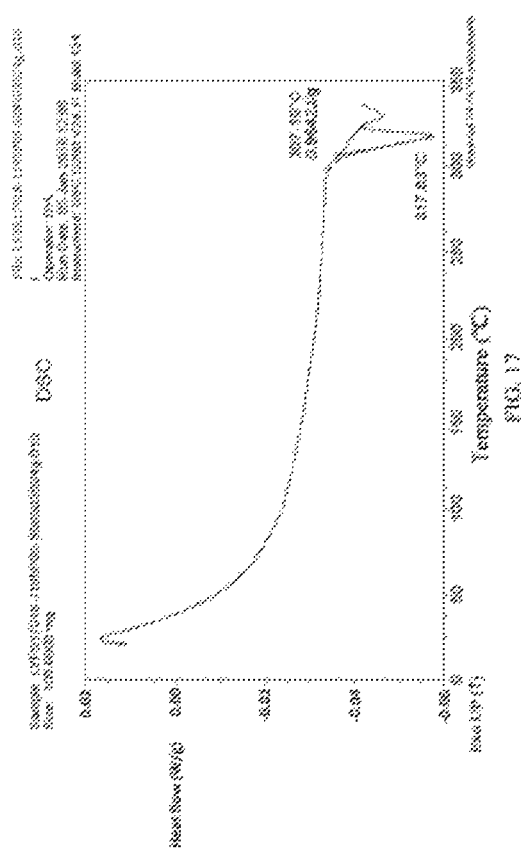
FIG. 17 illustrates differential scanning calorimetry (DSC) curves of the Crystalline Form I of 3-((L-valyl)amino)-1-propanesulfonic acid prepared in Example 14 of the present invention. In the DSC curves, the Crystalline Form I has a starting melt temperature of about 307° C. and a peak temperature of about 318° C. .
Figure 18:
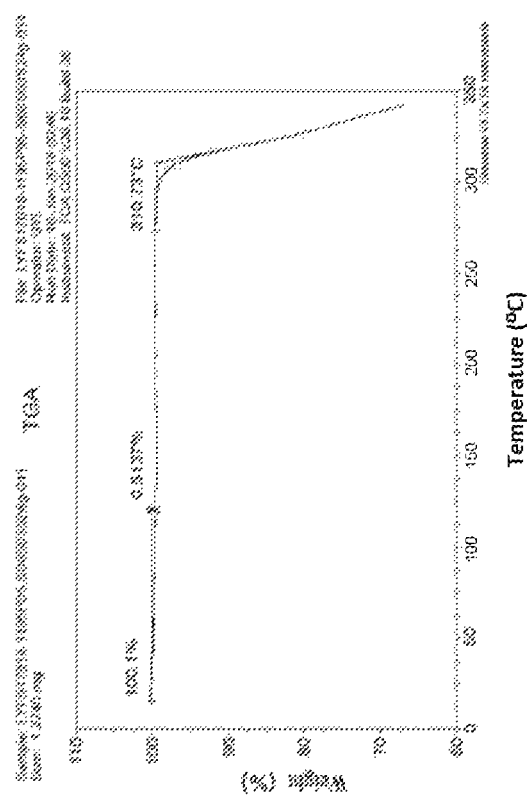
FIG. 18 is a thermogravimetric analysis diagram of the Crystalline Form I of 3-((L-valyl)amino)-1-propanesulfonic acid prepared in Example 14 of the present invention, which shows that the crystalline form has a slow weight loss of about 0.5wt % before about 120° C., showing that it is an anhydrate; and the decomposition temperature is about 310° C.

The DSC curves (see FIG.17) of the resulting crystal sample indicate that the starting melt temperature is about 307° C., and the peak temperature is about 318° C. The TGA diagram (see FIG.18) thereof shows that the crystalline form has a slow weight loss of about 0.5wt % before about 120° C., showing that it is an anhydrate; and the decomposition temperature is about 310° C.

EXAMPLES 15-23

Preparation of crystalline forms of 3-((L-valyl)amino)-1-propanesulfonic acid under different conditions by reference to the method of Example 14 was investigated, and results were shown in Table 5 below.

TABLE 5

The results of preparation of crystalline forms of 3-((L-valyl)amino)-1-propanesulfonic acid of examples 15-23

| Examples | Solvent System (First Solvent/Second Solvent/Third Solvent) | Amount of Solvents (v/v(ml/ml) or v/v/v, (ml/ml/ml)) | Amount of Amorphous Solid of Example 1 (mg) | Crystalline Form |
|---|---|---|---|---|
| 15 | Methanol/Acetone/Water | 2.0/2.0/0.2 | 15 | Crystalline Form I |
| 16 | N-propanol/Isopropyl Acetate/Water | 2.0/2.0/0.3 | 10 | Crystalline Form I |
| 17 | Acetone/Acetonitrile/Water | 2.0/2.0/0.2 | 10 | Crystalline Form I |
| 18 | Tetrahydrofuran/Methyl tert-butyl ether/Water | 2.0/1.0/0.2 | 10 | Crystalline Form I |
| 19 | Acetomtrile/Nitromethane/Water | 2.0/1.0/0.1 | 10 | Crystalline Form I |
| 20 | Water-saturated Sec-butanol | 2.0 | 10 | Crystalline Form I |
| 21 | Toluene/N-butanol | 1.0/1.0 | 10 | Crystalline Form I |
| 22 | Methylcyclohexane/Isopropanol | 1.0/1.0 | 10 | Crystalline Form I |
| 23 | ethanol | 2 | 10 | Crystalline Form I |

The crystal sample prepared in Examples 15-23 is the Crystalline Form I as characterized by XRD (not shown).

EXAMPLE 24

A solvent system of n-heptane/chloroform (1.0 mL/1.0 mL) having a total volume of 2 mL was added to 10 mg of the amorphous solid of 3-((L-valyl)amino)-1-propanesulfonic acid obtained according to Example 1, wherein solvents were added in the sequence of n-heptane (i.e., the first solvent) and chloroform (i.e., the second solvent) to obtain a suspension solution which was stirred for 5 days at a temperature of 40° C., and the resulting crystal slurry was subjected to centrifugal filtration, washing, and drying to obtain 9 mg of fine granular crystals, i.e., the Crystalline Form I as characterized by XRD (not shown), having a yield of 90% and a purity of greater than 99%.

Figure 19:
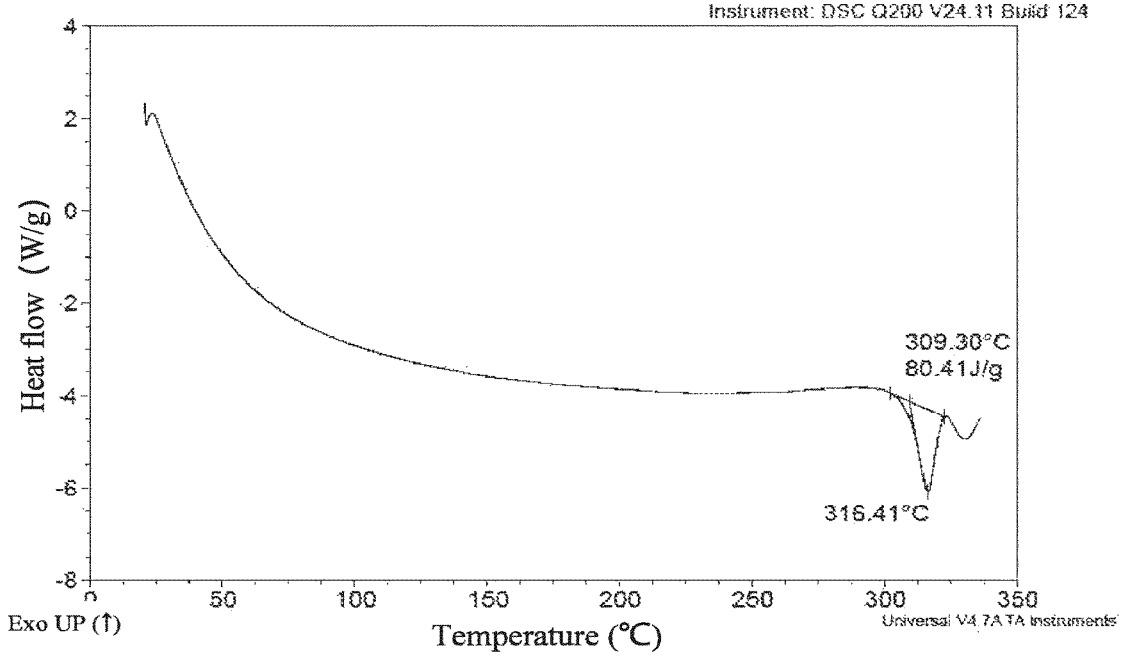
FIG. 19 illustrates differential scanning calorimetry (DSC) curves of the Crystalline Form I of 3-((L-valyl)amino)-1-propanesulfonic acid prepared in Example 24 of the present invention. In the DSC curves, the Crystalline Form I has a starting melt temperature of about 309° C. and a peak temperature of about 316° C.
Figure 20:
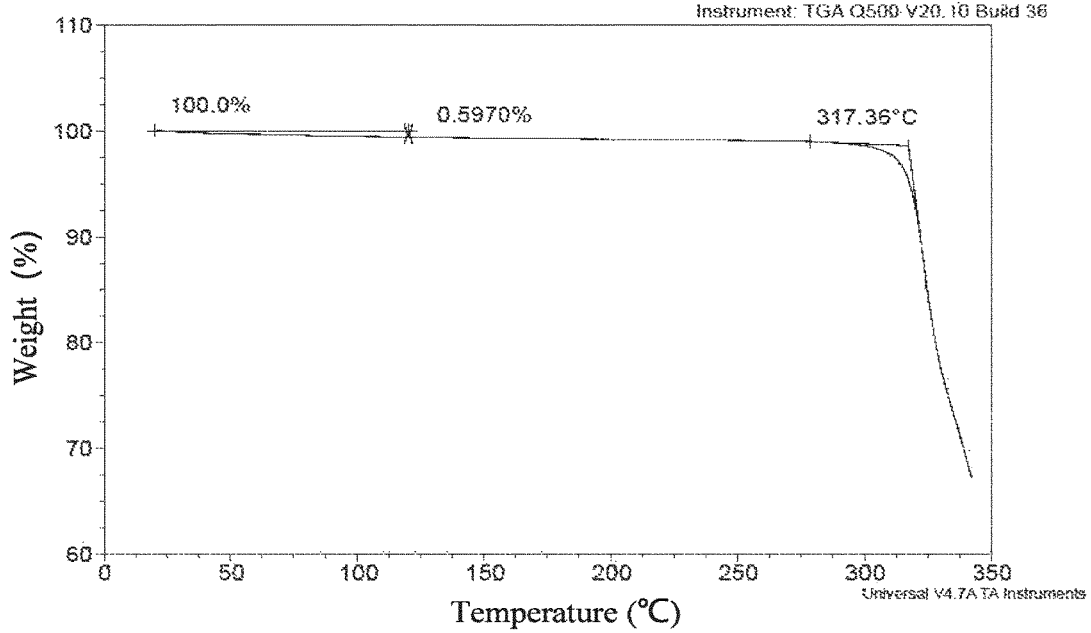
FIG. 20 is a thermogravimetric analysis diagram of the Crystalline Form I of 3-((L-valyl)amino)-1-propanesulfonic acid prepared in Example 24 of the present invention, which shows that the crystalline form has a slow weight loss of about 0.6wt % before about 120° C., showing that it is an anhydrate; and the decomposition temperature is about 317° C.
Figure 21:
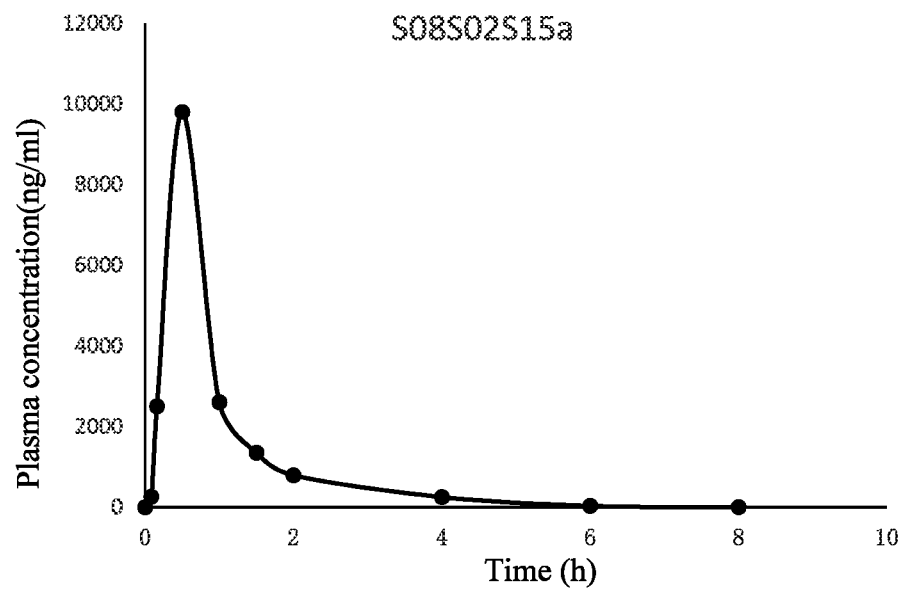
FIG. 21 is a blood concentration-time curve graph of the Crystalline Form I (No. S08S02S15a) of 3-((L-valyl)amino)-1-propanesulfonic acid prepared in Example 2 of the present invention.
Figure 22:
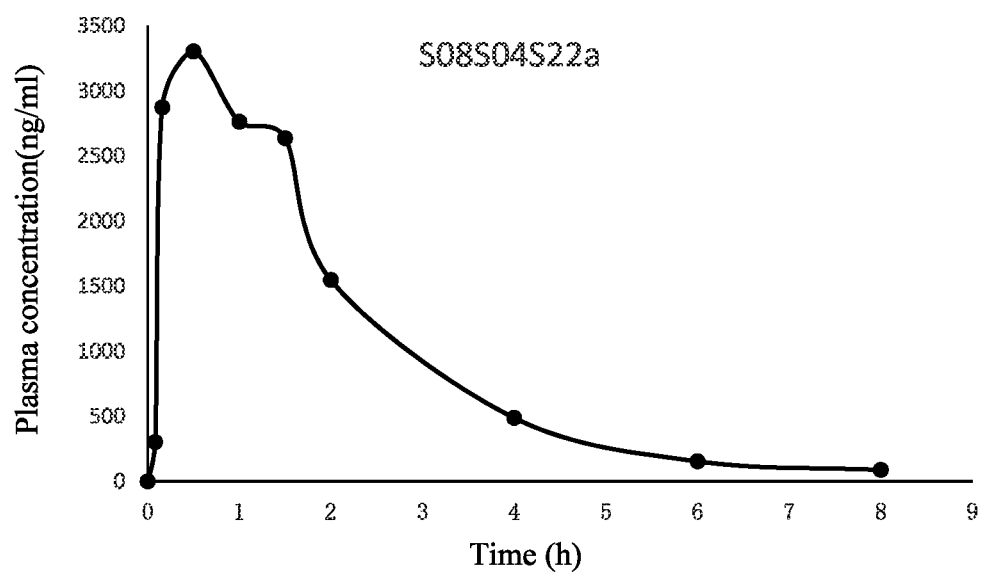
FIG. 22 is a blood concentration-time curve graph of the Crystalline Form I (No. S08S04S22a) of 3-((L-valyl)amino)-1-propanesulfonic acid prepared in Example 7 of the present invention.
Figure 23:
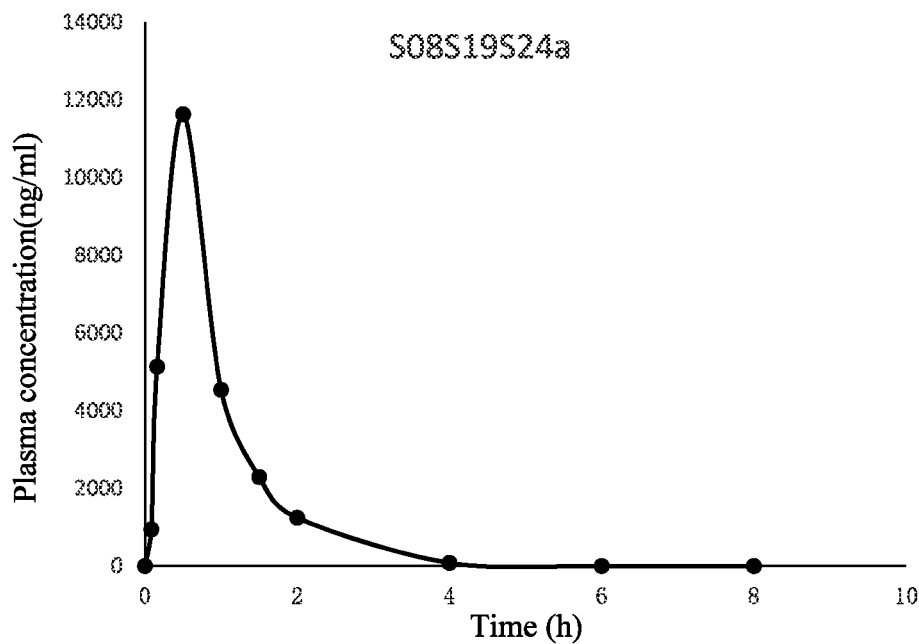
FIG. 23 is a blood concentration-time curve graph of the Crystalline Form I (No. S08S19S24a) of 3-((L-valyl)amino)-1-propanesulfonic acid prepared in Example 8 of the present invention.
Figure 24:
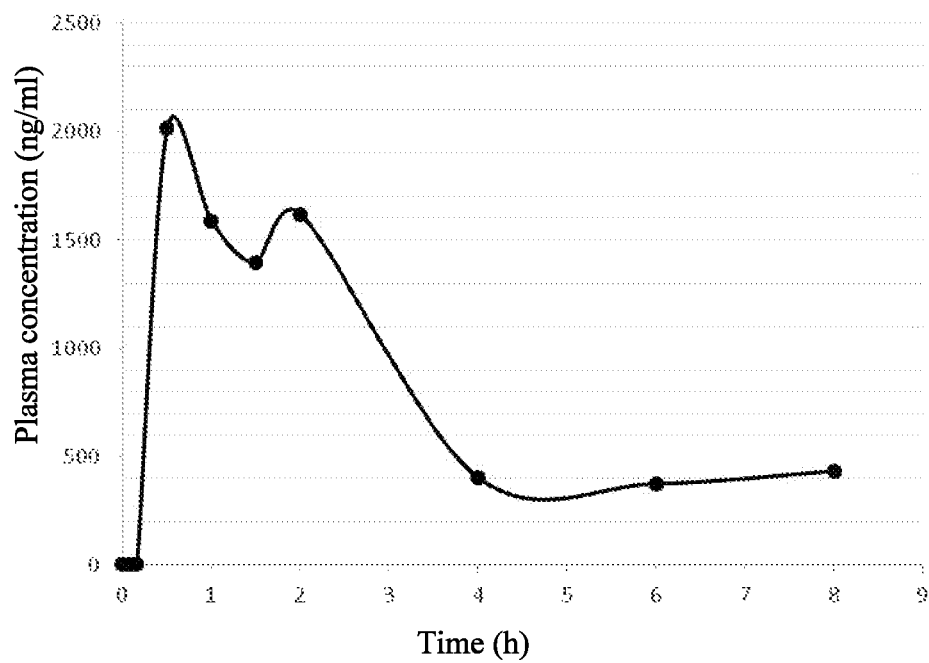
FIG. 24 is a blood concentration-time curve graph of an amorphous form solid of Example 1 as a reference sample.

The DSC curves (see FIG. 19) of the resulting crystal sample indicate that the starting melt temperature is about 309° C., and the peak temperature is about 316° C. The TGA diagram (see FIG. 20) thereof shows that the crystalline form has a slow weight loss of about 0.6wt % before about 120° C., showing that it is an anhydrate; and the decomposition temperature is about 317° C.

EXAMPLES 25-31

Preparation of crystalline forms of 3-((L-valyl)amino)-1-propanesulfonic acid under different conditions by reference to the method of Example 24 was investigated, and results were shown in Table 6 below.

TABLE 6

The results of preparation of crystalline forms of 3-((L-valyl)amino)-1-propanesulfonic acid of examples 25-31

| Examples | Solvent System (First Solvent/Second Solvent/ optional Third Solvent) | Amount of Solvents (v/v(ml/ml) or v/v/v, (ml/ml/ml)) | Amount of Amorphous Solid of Example 1 (mg) | Crystalline Form |
|---|---|---|---|---|
| 25 | Water-saturated Ethyl Acetate | 2.0 | 15 | Crystalline Form I |
| 26 | Isopropanol | 2.0 | 10 | Crystalline Form I |
| 27 | Ethanol/Butanone/Water | 2.0/2.0/0.2 | 10 | Crystalline Form I |
| 28 | N-butanol/Acetic Acid/Water | 2.0/2.0/0.1 | 10 | Crystalline Form I |
| 29 | 1,4-dioxane/Isopropyl acetate/Water | 2.0/2.0/0.2 | 10 | Crystalline Form I |
| 30 | Isopropyl Ether/Acetonitrile | 1.0/1.0 | 10 | Crystalline Form I |
| 31 | Tetrahydrofuran/Methanol | 1.0/1.0 | 10 | Crystalline Form I |

The crystal sample prepared in Examples 25-31 is the Crystalline Form I as characterized by XRD (not shown).

EXAMPLE 32

A solvent system of methanol/water/acetone (0.09 mL/0.09 mL/4.0 mL) having a total volume of 4.18 mL was added to 10 mg of the amorphous solid of 3-((L-valyl)amino)-1-propanesulfonic acid obtained according to Example 1, wherein solvents were added in the sequence of methanol (i.e., the first solvent) and water (i.e., the second solvent) to obtain a clear solution, and acetone (i.e., the third solvent) was slowly added during stirring. Stirring continues for 3 min after precipitation of the solid, and the resulting crystal slurry was subjected to centrifugal filtration, washing, and drying to obtain 9 mg of crystals, i.e., the Crystalline Form I as characterized by XRD (not shown), having a yield of 90% and a purity of greater than 99%.

EXAMPLES 33-40

Preparation of crystalline forms of 3-((L-valyl)amino)-1-propanesulfonic acid under different conditions by reference to the method of Example 32 was investigated, and results were shown in Table 7 below.

TABLE 7

The results of preparation of crystalline forms of 3-((L-valyl)amino)-1-propanesulfonic acid of examples 33-40

| Examples | Solvent System (First Solvent/Second Solvent/ optional Third Solvent) | Amount of Solvents (v/v(ml/ml) or v/v/v, (ml/ml/ml)) | Amount of Amorphous Solid of Example 1 (mg) | Crystalline Form |
|---|---|---|---|---|
| 33 | Trifluoroethanol/Water/Acetonitrile | 0.09/0.09/2.0 | 10 | Crystalline Form I |
| 34 | N-propanol/Water/Tetrahydrofuran | 0.09/0.09/2.0 | 10 | Crystalline Form I |
| 35 | acetone/Water/Isopropanol | 0.09/0.09/2.0 | 10 | Crystalline Form I |
| 36 | Tetrahydrofuran/Water/N-butanol | 0.09/0.09/2.0 | 10 | Crystalline Form I |
| 37 | ethanol/Water/N,N-dimethylformamid | 0.09/0.09/5.0 | 10 | Crystalline Form I |
| 38 | Isopropanol/Water/1,4-dioxane | 0.09/0.09/2.0 | 10 | Crystalline Form I |
| 39 | 1,4-dioxane/Water/ethanol | 0.09/0.09/5.0 | 10 | Crystalline Form I |
| 40 | Acetonitrile/Water/Acetic Acid | 0.09/0.09/5.0 | 10 | Crystalline Form I |

The crystal sample prepared in Examples 33-40 is the Crystalline Form I as characterized by XRD (not shown)

EXAMPLE 41

To 15 mg of the amorphous solid of 3-((L-valyl)amino)-1-propanesulfonic acid in Example 1 a solvent system of water/ethanol/1,4-dioxane (0.2 mL/1.0 mL/0.8 mL) having a total volume of 2 mL was added at a temperature of 60° C., wherein solvents were added in the sequence of water (i.e., the first solvent), ethanol (i.e., the second solvent), and 1,4-dioxane (i.e., the third solvent) to obtain a clear solution, which was then placed in ice-salt baths and stirred.

After precipitation of the solid, the resulting crystal slurry was subjected to centrifugal filtration, washing, and drying to obtain 13 mg of crystals, i.e., the Crystalline Form I as characterized by XRD (not shown), having a yield of 87% and a purity of greater than 99%.

EXAMPLE 42

To 15 mg of the amorphous solid of 3-((L-valyl)amino)-1-propanesulfonic acid in Example 1 a solvent system of water/isopropanol/tetrahydrofuran (0.2 mL/1.0 mL/0.6 mL) having a total volume of 1.8 mL was added at a temperature of 60° C., wherein solvents were added in the sequence of water (i.e., the first solvent), isopropanol (i.e., the second solvent), and tetrahydrofuran (i.e., the third solvent) to obtain a clear solution, which was then placed in ice-salt baths and stirred. After precipitation of the solid, the resulting crystal slurry was subjected to centrifugal filtration, washing, and drying to obtain 14 mg of crystals, i.e., the Crystalline Form I as characterized by XRD (not shown), having a yield of 93% and a purity of greater than 99%.

EXAMPLES 43-48

Preparation of crystalline forms of 3-((L-valyl)amino)-1-propanesulfonic acid under different conditions by reference to the method of Example 41 was investigated, and results were shown in Table 8 below.

TABLE 8

The results of preparation of crystalline forms of 3-((L-valyl)amino)-1-propanesulfonic acid of examples 43-48

| Examples | Solvent System (First Solvent/Second Solvent/ optional Third Solvent) | Amount of Solvents (v/v(ml/ml) or v/v/v, (ml/ml/ml)) | Amount of Amorphous Solid of Example 1 (mg) | Crystalline Form |
|---|---|---|---|---|
| 43 | Water/Methanol/Acetonitrile | 0.2/1.0/1.0 | 15 | Crystalline Form I |
| 44 | Water/Trifluoroethanol/Acetone | 0.2/1.0/1.0 | 15 | Crystalline Form I |
| 45 | Water/Acetone/Ethyl Acetate | 0.2/0.6/0.4 | 15 | Crystalline Form I |
| 46 | Dimethyl Sulfoxide/Chloroform/N-butanol | 1.0/1.0/1.0 | 15 | Crystalline Form I |
| 47 | Dimethyl Sulfoxide/Butanone/Toluene | 1.0/1.0/1.0 | 15 | Crystalline Form I |
| 48 | Dimethyl Sulfoxide/Acetonitrile/Isopropyl Acetate | 1.0/2.0/2.0 | 15 | Crystalline Form I |

EXAMPLE 49

10 mg of the amorphous solid of 3-((L-valyl)amino)-1-propanesulfonic acid in Example 1 was taken and placed in a centrifuge tube, 0.05 mL of water was added, and then the solution was allowed to stand in an atmosphere of tetrahydrofuran to precipitate a solid to obtain 9 mg of crystals, i.e., the Crystalline Form I as characterized by XRD (not shown), having a yield of 90% and a purity of greater than 99%.

EXAMPLE 50

10 mg of the amorphous solid of 3-((L-valyl)amino)-1-propanesulfonic acid in Example 1 was taken and placed in a centrifuge tube, 0.05 mL of water was added, and then the solution was allowed to stand in an atmosphere of methanol to precipitate a solid to obtain 9 mg of crystals, i.e., the Crystalline Form I as characterized by XRD (not shown), having a yield of 90% and a purity of greater than 99%.

EXAMPLE 51

Pharmacokinetics Comparative Analysis

By means of a pharmacokinetics comparative experiment, the pharmacodynamics feature of the crystalline form I provided herein after administration is compared with that of the amorphous solid of Example 1 as a reference sample.

Experimental Method:

SD rats (all male, weight of 260-280 g) were randomizely grouped, each group of 3 animals. The medication group received the crystalline form compound (No. S08S02S15a) of the Example 2, the crystalline form compound (No. S08S04S22a) of the Example 7, and the crystalline form compound (No. S08S19S24a) of the Example 8, respectively, and the control group received the reference sample (the amorphous solid of Example 1). The animals were fasted for 12 hours before administration, and the dosage of administration was 133 mg/kg. The corresponding medications were administered by intragastric administration using a solid capsule administration system (Size 9el Rat Box+Foam+Funnel+Syringe). Rat plasma samples were collected before administration, and 0.08, 0.16, 0.33, 0.5, 1, 1.5, 2, 3, 4, 6, and 8 h after administration, respectively. After heparin tube anticoagulation, centrifugation was performed at 5000 rpm for 10 min at a temperature of 4° C. A plasma supernatant sample was taken and subjected to protein precipitation using methanol, and then, the medication concentration in the plasma was monitored by LC/MS2. A blood concentration-time curve is plotted for the results, as shown in FIGS. 21-24.

As can be seen from FIGS. 21-24, as compared with the reference sample, the compound of the Crystalline Form I provided herein is capable of improving medication dissolution. Without being bound by theory, the inventor believes that during capsule intragastric administration, the medication of the crystalline form I provided herein can effectively improve the maximum blood concentration $C_{max}$, exposure AUC, half-life period $T_{1/2}$, etc., and has certain advantages in medication dissolution, due to physical properties such as crystal form, particle size, and uniformity, which are different from and superior to those of the amorphous solid.

The present invention is not limited by the examples shown and described above, but may vary within the scope of the claims.

Unless defined otherwise or the context clearly dictates otherwise, all technical and scientific terms used herein have the same meaning as commonly understood by one of ordinary skill in the art to which this invention belongs. It should be understood that any methods and materials similar or equivalent to those described herein can be used in the practice or testing of the invention.

What is claimed is:

1. A crystalline form of 3-((L-valyl)amino)-1-propanesulfonic acid, characterized in that said crystalline form exhibits characteristic diffraction peaks at 2θ diffraction angles of 9.4°, 11.1°, 15.9°, 17.8°, 18.4°, 21.0°, and 22.5° in an X-ray powder diffraction pattern using Cu-Kα as a radiation source, wherein 2θ has an error range of ±0.2°, and a starting melt temperature of a differential scanning calorimetry curve of said crystalline form is about 301° C. or higher.

2. The crystalline form of claim 1, wherein the starting melt temperature of the differential scanning calorimetry curve of said crystalline form is about 301° C. to about 312° C.

3. The crystalline form of claim 1, wherein said crystalline form exhibits characteristic diffraction peaks at 2θ diffraction angles of 9.4°, 11.1°, 14.9°, 15.9°, 16.6°, 17.8°, 18.4°, 19.5°, 21.0°, 22.5°, 23.1°, and 25.7° in the X-ray powder diffraction pattern, wherein 2θ has an error range of ±0.2°.

4. The crystalline form of claim 1, wherein said crystalline form exhibits characteristic diffraction peaks at 2θ diffraction angles of 9.4°, 11.1°, 14.9°, 15.9°, 16.6°, 17.8°, 18.4°, 19.5°, 20.2°, 21.0°, 21.6°, 22.5°, 23.1°, 25.7°, 26.4°, 26.9°, 30.4°, 32.4°, and 34.5° in the X-ray powder diffraction pattern, wherein 2θ has an error range of ±0.2°.

5. The crystalline form of claim 1, wherein said crystalline form has a space group of P4₃2₁2, unit cell dimensions: a=11.1989(4) Å, α=90°, b=11.1988(4) Å, β=90°, c=18.2429(7) Å, γ=90°, Z=8, and has a unit cell volume of 2287.90(19) Å³.

6. The crystalline form of claim 5, wherein said crystalline form belongs to a tetragonal system.

7. The crystalline form of claim 6, wherein said crystalline form has a crystal size of 0.300×0.300×0.100 mm³.

8. A method for preparing the crystalline form of compound 3-((L-valyl)amino)-1-propanesulfonic acid of claim 1, characterized in that said method comprises the following steps:
adding a solvent system to the compound 3-((L-valyl)amino)-1-propanesulfonic acid to obtain a clear solution, and volatilizing to dryness to obtain said crystalline form, wherein the step of adding the solvent system comprises:
adding the solvent system consisting of a first solvent, wherein said first solvent is water; or
adding the solvent system consisting of a first solvent and a second solvent, wherein said first solvent is firstly added, followed by said second solvent, wherein said first solvent is water, and said second solvent is selected from the group consisting of methanol or halogenated fatty alcohol; or
adding the solvent system comprising or consisting of a first solvent, a second solvent, and a third solvent, wherein said first solvent is firstly added, sequentially followed by said second solvent and said third solvent, wherein said first solvent is water, and a combination of said second solvent/said third solvent is alcohols/ketones, alcohols/ethers, esters/nitriles, ketones/esters, or nitriles/N,N-dimethylformamide.

9. The method of claim 8, wherein:
said alcohols are selected from the group consisting of methanol, ethanol, n-propanol, isopropanol, n-butanol, sec-butanol, pentanol, and hexanol; said ketones are selected from the group consisting of acetone, butanone, and 2-pentanone; said ethers are selected from the group consisting of ethyl ether, isopropyl ether, methyl tert-butyl ether, tetrahydrofuran, or 1,4-dioxane; said esters are selected from the group consisting of ethyl formate, propyl formate, isopropyl formate, methyl acetate, ethyl acetate, and isopropyl acetate; and said nitriles are selected from the group consisting of acetonitrile, propionitrile, butyronitrile, and isobutyronitrile; or
wherein the solvent system consisting of said first solvent and said second solvent is added to said compound, wherein said first solvent is firstly added, followed by said second solvent, wherein said first solvent is water, and said second solvent is selected from methanol or trifluoroethanol, or
wherein the solvent system consisting of said first solvent, said second solvent and said third solvent is added to said compound, wherein said first solvent is firstly added, sequentially followed by said second solvent and said third solvent, wherein said first solvent is water, said second solvent is different from said third solvent, and a combination of said second solvent/said third solvent is ethanol/acetone, isopropanol/tetrahydrofuran, ethyl acetate/acetonitrile, n-propanol/1,4-dioxane, acetone/isopropyl acetate, or acetonitrile/N,N-dimethylformamide,
wherein a volume ratio of said first solvent to said second solvent is 1:0.01-1:200 or 1:0.5-1:20,
wherein a volume ratio of said first solvent to said second solvent to said third solvent is 1:0.01-200:0.01-200 or 1:0.1-20:0.1-20.

10. The method of claim 8, wherein said clear solution is allowed to stand at room temperature or at a temperature of about 10-30° C. or at a crystallization temperature of about 20-60° C. or about 40-60° C. until it volatizes to dryness to obtain said crystalline form.

11. The method of claim 8, wherein a mass-to-volume ratio of said compound to the total solvent is:
10 mg:0.05 ml-100 mg:250 ml or 100 mg:0.5 ml-100 mg:50 ml.

12. A method for preparing the crystalline form of compound 3-((L-valyl)amino)-1-propanesulfonic acid of claim 1, characterized in that said method comprises the following steps:
adding a solvent system to the compound 3-((Lvalyl)amino)-1-propanesulfonic acid to obtain a suspension solution, and stirring to obtain said crystalline form, wherein the step of adding the solvent system comprises:

adding the solvent system consisting of a first solvent, wherein said first solvent is selected from a group consisting of ethanol, isopropanol, propanol, water-saturated secbutanol, or water-saturated esters solvent; or adding the solvent system consisting of a first solvent and a second solvent, wherein said first solvent is firstly added, followed by said second solvent, wherein said first solvent is different from said second solvent, and a combination of said first solvent/said second solvent is aromatics solvent/alcohols, alicyclic hydrocarbons solvent/alcohols, ethers/nitriles, alkanes solvent/halogenated alkanes solvent, or ethers/alcohols; or adding the solvent system comprising or consisting of a first solvent, a second solvent, and a third solvent, wherein said first solvent is firstly added, sequentially followed by said second solvent and said third solvent, wherein said third solvent is water, said first solvent is different from said second solvent, and a combination of said first solvent/said second solvent is alcohols/ketones, halogenated fatty alcohols/nitriles, alcohols/esters, ketones/nitriles, first ethers/second ethers, nitriles/nitromethane, alcohols/fatty acids, or ethers/esters.

13. The method of claim 12, wherein said suspension solution is stirred to crystallize at a crystallization temperature of about 10-60° C.

14. A method for preparing the crystalline form of compound 3-((L-valyl)amino)-1-propanesulfonic acid of claim 1, characterized in that said method comprises the following steps:

adding a first solvent and a second solvent to the compound 3-((L-valyl)amino)-1-propanesulfonic acid to obtain a clear solution, adding a third solvent under stirring, and crystallizing to obtain said crystalline form, wherein a combination of said first solvent/said second solvent/said third solvent is alcohols/water/ketones, halogenated fatty alcohols/water/nitriles, ketones/water/alcohols, ethers/water/alcohols, alcohols/water/N,N-dimethylformamide, alcohols/water/ethers, first alcohols/water/second alcohols, or nitriles/water/fatty acids, wherein said first alcohols differ from said second alcohols.

15. A method for preparing the crystalline form of compound 3-((L-valyl)amino)-1-propanesulfonic acid of claim 1, characterized in that said method comprises the following steps: adding a solvent to the compound 3-((L-valyl)amino)-1-propanesulfonic acid at a temperature of about 30-80° C. to obtain a clear solution, cooling, and crystallizing to obtain said crystalline form, wherein the step of adding said solvent comprises:

firstly adding a first solvent, followed by sequentially adding a second solvent and a third solvent, wherein said first solvent is water or dimethyl sulfoxide, and a combination of said second solvent/said third solvent is alcohols/nitriles, alcohols/ethers, halogenated fatty acids/ketones, ketones/esters, halogenated alkanes/alcohols, ketones/aromatics, or nitriles/esters.

16. The method of claim 15, wherein said crystallizing is performed at a temperature of about −20-10° C.

17. A pharmaceutical composition comprising the crystalline form of compound 3-((Lvalyl)amino)-1-propanesulfonic acid of claim 1, and a pharmaceutically acceptable carrier.

18. A method of prevention or treatment of an amyloid-β related disease in a subject in need thereof comprising administrating to the subject a therapeutically effective amount of the crystalline form of 3-((L-valyl)amino)-1-propanesulfonic acid of claim 1.

19. The method of claim 18, wherein said amyloid-β related disease is Alzheimer's disease, mild cognitive impairment (MCI), Down's syndrome, Hereditary Cerebral Hemorrhage with Amyloidosis of the Dutch-Type, cerebral amyloid angiopathy, a degenerative dementia, a dementia of mixed vascular and degenerative origin, dementia associated with Parkinson's disease, dementia associated with progressive supranuclear palsy, dementia associated with cortical basal degeneration, or dementia associated with diffuse Lewy body type of Alzheimer's disease.

20. The method of claim 18, wherein said subject is an ApoE4 positive subject.

* * * * *